US012280011B1

(12) United States Patent
Nelson et al.

(10) Patent No.: US 12,280,011 B1
(45) Date of Patent: Apr. 22, 2025

(54) MULTI-VIAL ADAPTERS FOR RECONSTITUTING OR DILUTING LYOPHILIZED OR CONCENTRATED DRUG PRODUCTS

(71) Applicant: GENZYME CORPORATION, Cambridge, MA (US)

(72) Inventors: Craig Nelson, Melbourne (GB); Alexander Hee-Hanson, Melbourne (GB); Tom Lever, Melbourne (GB); Haiming Wu, Cambridge, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 18/627,596

(22) Filed: Apr. 5, 2024

(51) Int. Cl.
*A61J 1/20* (2006.01)
*A61J 1/22* (2006.01)
*A61M 37/00* (2006.01)

(52) U.S. Cl.
CPC .......... *A61J 1/2048* (2015.05); *A61J 1/2006* (2015.05); *A61J 1/2079* (2015.05); *A61J 1/2096* (2013.01); *A61J 1/22* (2013.01); *A61M 37/0015* (2013.01)

(58) Field of Classification Search
CPC ...... A61J 1/2096; A61J 1/2058; A61J 1/2017; A61J 1/2089; A61J 1/2003
See application file for complete search history.

(56) References Cited

U.S. PATENT DOCUMENTS

| | | | |
|---|---|---|---|
| 6,210,361 B1 | 4/2001 | Kamen et al. | |
| 9,237,985 B2 | 1/2016 | Eckhoff et al. | |
| 9,662,621 B2 | 5/2017 | Beyer et al. | |
| 11,497,685 B2 | 11/2022 | McLoughlin et al. | |
| 2015/0297831 A1 | 10/2015 | Patrick et al. | |
| 2017/0336141 A1 | 11/2017 | Schuetz et al. | |
| 2021/0154097 A1 | 5/2021 | McLoughlin et al. | |

(Continued)

FOREIGN PATENT DOCUMENTS

| AU | 2014280875 B2 | 1/2015 |
|---|---|---|
| EP | 3790525 B1 | 3/2024 |

(Continued)

OTHER PUBLICATIONS

Machine translation of WO 97/20536 Meyer (Year: 1997).*

(Continued)

*Primary Examiner* — Leslie R Deak
(74) *Attorney, Agent, or Firm* — Bond, Schoeneck & King, PLLC

(57) ABSTRACT

The present disclosure is directed to adapters for mixing vials of drug products, and more specifically to multi-vial adapters for reconstituting lyophilized drug products and/or diluting concentrated drug products. It is an object to address one or more of drawbacks in connection with the drug preparation process, for example, by simplifying the procedure where multiple vials are required to be diluted or reconstituted in a serial manner. As such, the multi-vial adapters described herein simplify the complexity of preparing and handling multiple vials of drug product, which significantly reduces preparation time, addresses dosing-related challenges like weight-based preparation, reduces drug waste issues, and reduces risks associated sterility and contamination, among other benefits.

15 Claims, 16 Drawing Sheets

(56) References Cited

U.S. PATENT DOCUMENTS

| | | |
|---|---|---|
| 2021/0369958 A1 | 12/2021 | Jones et al. |
| 2022/0023531 A1 | 1/2022 | McLoughlin et al. |
| 2022/0202648 A1 | 6/2022 | Berger et al. |
| 2022/0370289 A1 | 11/2022 | McLoughlin et al. |
| 2023/0149264 A1* | 5/2023 | Park ................ A61J 1/2055 604/411 |
| 2023/0311083 A1 | 10/2023 | Demers et al. |
| 2024/0123137 A1 | 4/2024 | Ryan |

FOREIGN PATENT DOCUMENTS

| | | | |
|---|---|---|---|
| KR | 20240019809 A | 2/2024 | |
| WO | WO-9720536 A1 * | 6/1997 | ............ A61J 1/2089 |
| WO | 2007101784 A1 | 9/2007 | |
| WO | WO-2008053462 A2 * | 5/2008 | ................ A61J 1/20 |
| WO | WO-2019217820 A1 * | 11/2019 | ............. A61J 1/065 |

OTHER PUBLICATIONS

European Search Report, EP Application No. 24168810.0, dated Sep. 30, 2024, pp. 1-8.
European Search Report, EP Application No. 24168811.8, dated Aug. 8, 2024, pp. 1-10.

* cited by examiner

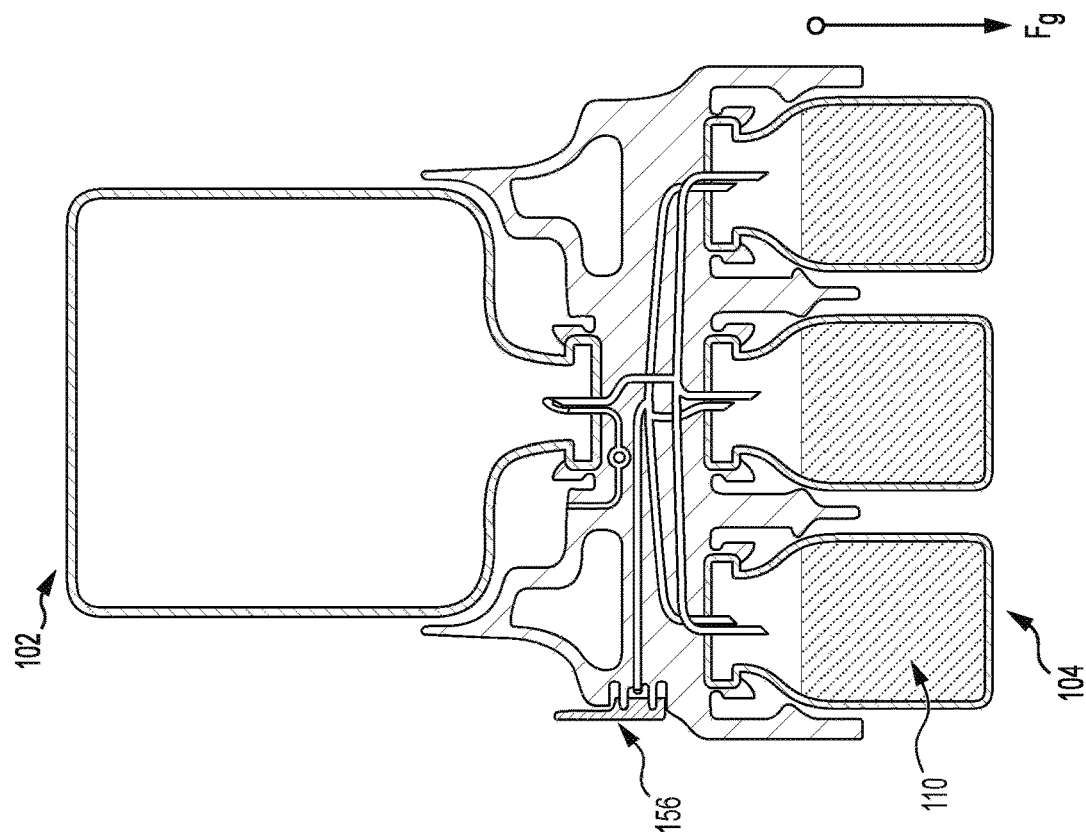
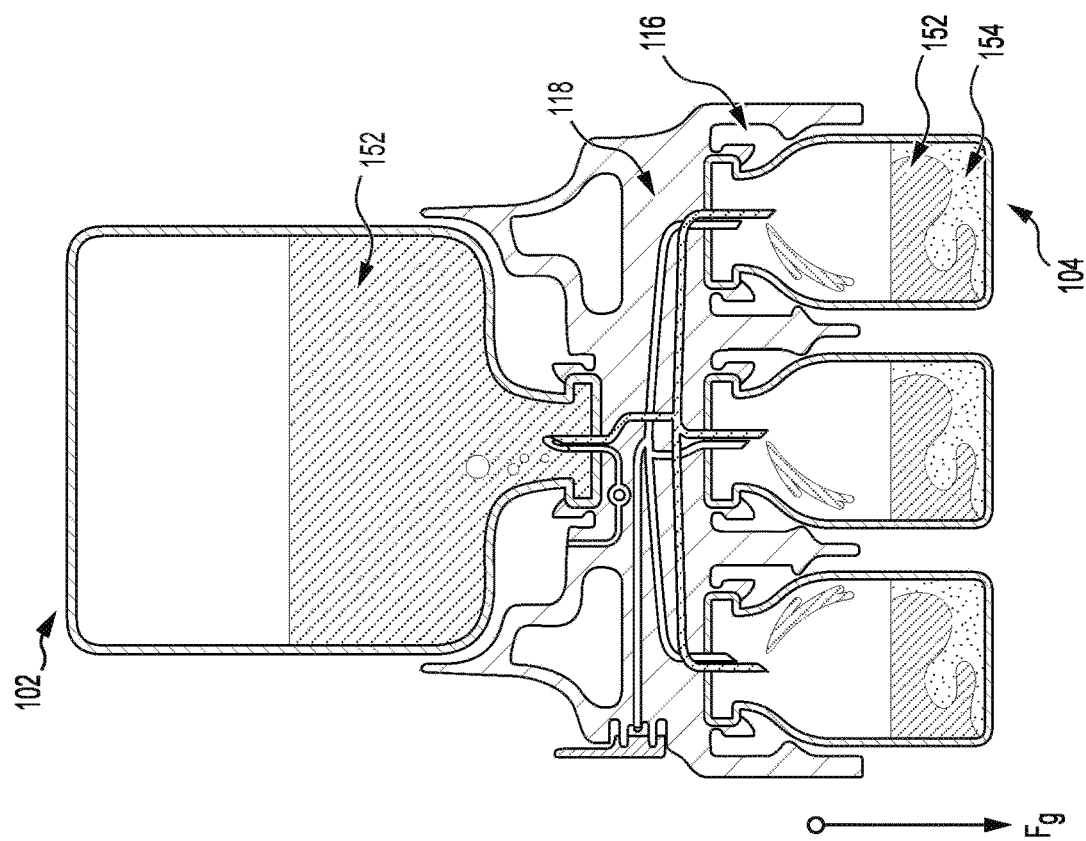

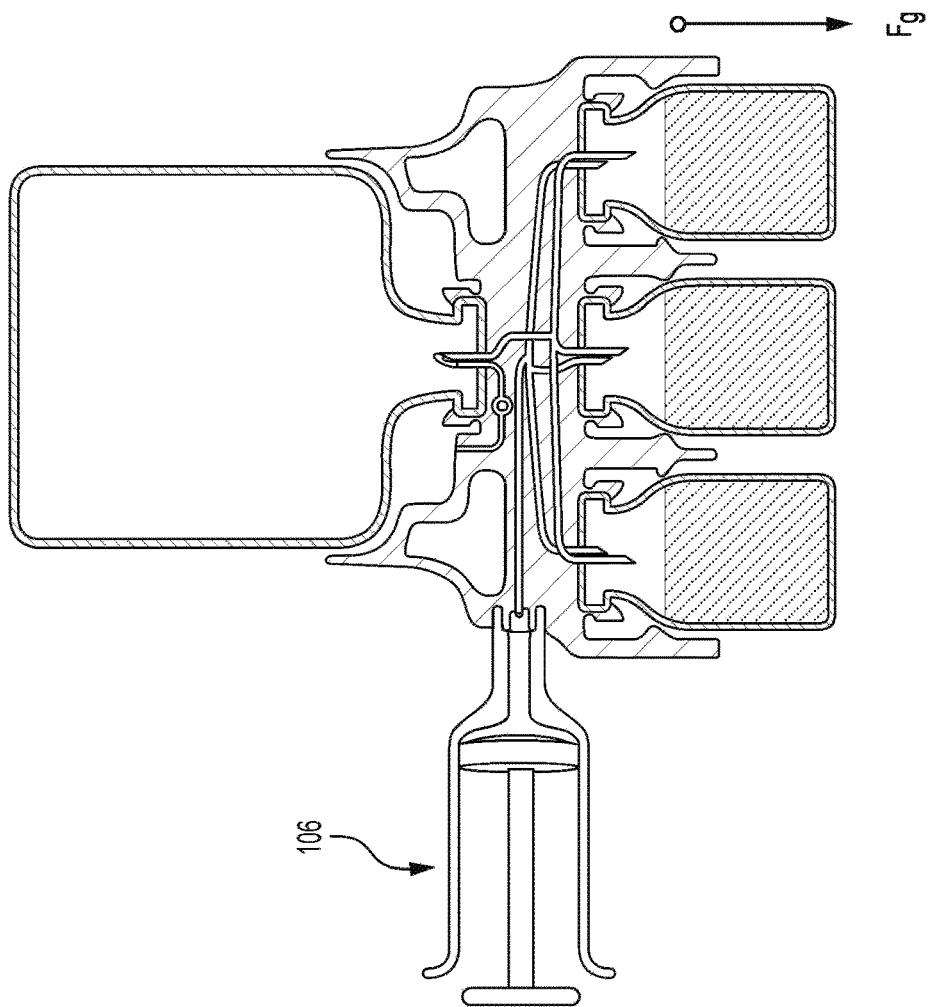
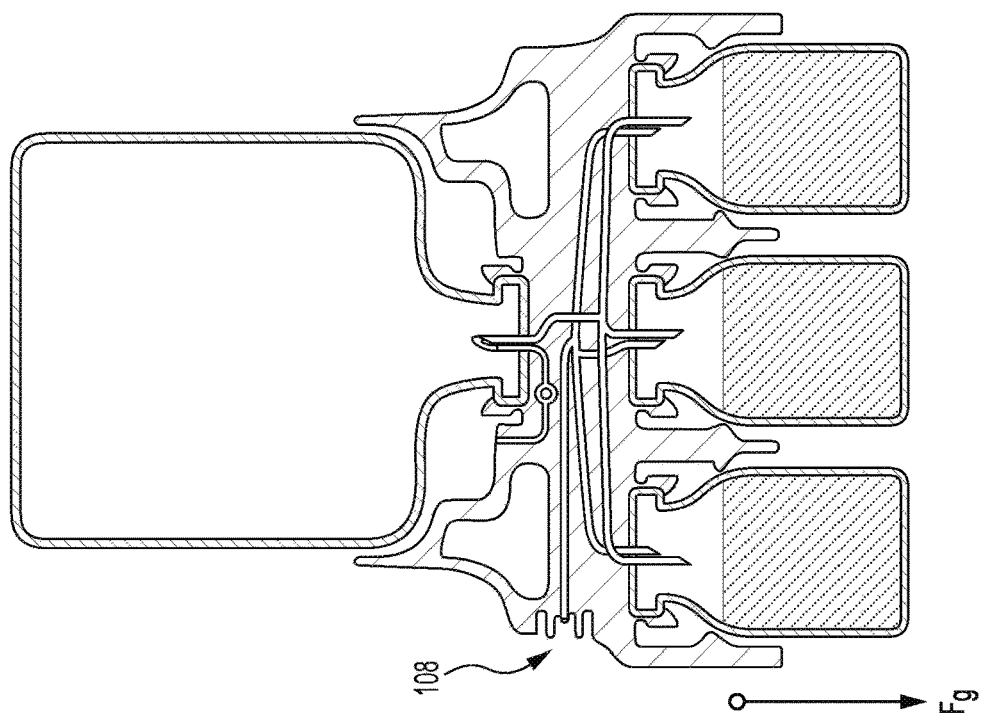

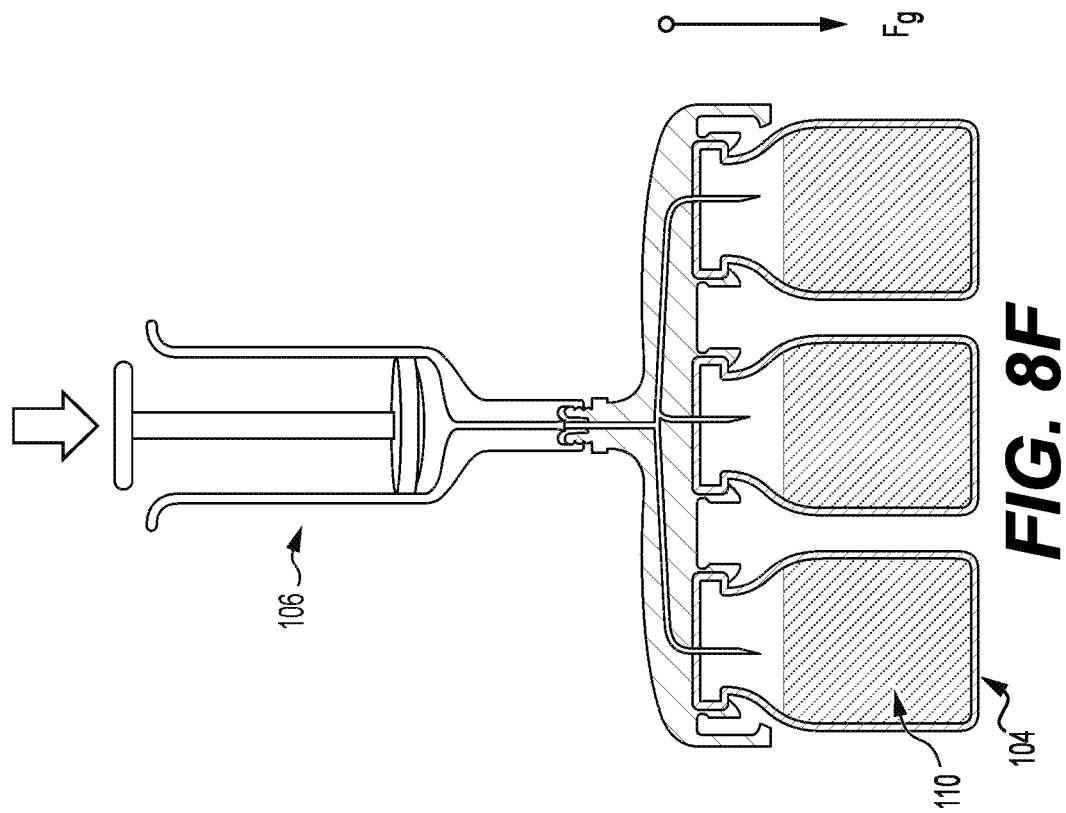
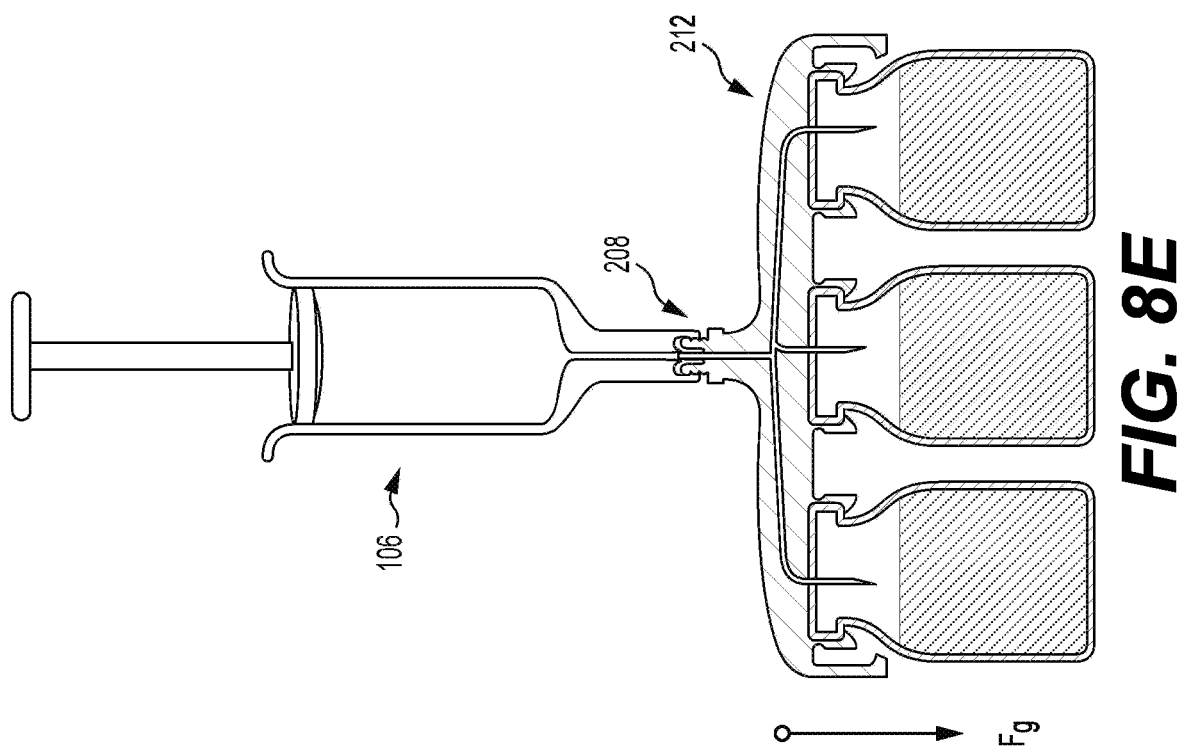

MULTI-VIAL ADAPTERS FOR RECONSTITUTING OR DILUTING LYOPHILIZED OR CONCENTRATED DRUG PRODUCTS

TECHNICAL FIELD

The present disclosure relates generally to adapters for mixing vials of drug products, and more specifically to multi-vial adapters for reconstituting lyophilized drug products and/or diluting concentrated drug products.

BACKGROUND

Patients suffering from certain diseases, like, for example, hemophilia or requiring enzyme replacement therapy, have to take regular intravenous (IV) infusions. These infusions have to be mixed and prepared, sometimes to the specific needs of the patient and sometimes a short time before drug administration. Oftentimes, this process involves reconstituting and/or diluting a lyophilized and/or concentrated drug product. In some cases, it is necessary to combine multiple vials of a drug product with a liquid diluent in order to obtain the proper concentration and dosage. Depending on how the manufacturer packages the drug product, the preparation process may require diluting and/or reconstituting dozens of vials of a drug product. In such cases, the complexity of preparing and handling the drug product increases exponentially, resulting in significantly extended preparation times, dosing-related challenges like weight-based preparation, drug waste due to dead volume, and risks associated with potential contamination. Because this preparation process is complex and tedious, it is usually performed by a healthcare professional in a clinic or pharmacy using specialized lab equipment. As such, while many patients would prefer the convenience of self-medication or home-medication for administering a medicament through infusion or injection, this remains a significant challenge.

Thus, it is desirable to ensure safe and precise reconstitution of drug products by facilitating aseptic transfer of diluent into one or more vials containing lyophilized or powdered drug products, thereby preventing contamination, attaining accurate dosage preparation, and maintaining sterility throughout the reconstitution process, ultimately enhancing the safety and efficacy of the administered medication.

SUMMARY OF THE DISCLOSURE

The present disclosure is directed to adapters for mixing vials of drug products, and more specifically to multi-vial adapters for reconstituting lyophilized drug products and/or diluting concentrated drug products. It is an object of the present disclosure to address one or more of drawbacks discussed above in connection with the drug preparation process, including by simplifying the procedure where multiple vials are required to be diluted or reconstituted in a serial manner. These and other benefits will become apparent those of ordinary skill in the relevant arts based on the present disclosure.

According to an embodiment of the present disclosure, a multi-vial adapter configured to reconstitute or dilute a lyophilized or concentrated drug product is provided. The multi-vial adapter may include: an adapter body having a primary interface configured to receive a diluent source and two or more secondary interfaces configured to receive two or more drug product vials. The adapter body may define a plurality of fluid paths through the adapter body that fluidly connect the primary interface with the two or more secondary interfaces. The diluent source may be either a diluent vial or a pre-filled syringe.

In an aspect, the diluent source may be a diluent vial and the adapter body may include at least one hollow needle disposed within a recess of the primary interface such that the at least one hollow needle is fluidly connected to the plurality of fluid paths. The at least one hollow needle may be configured to puncture a top of the diluent vial when received by the primary interface.

In an aspect, the adapter body may include at least one hollow needle disposed within each of the two or more secondary interfaces such that each hollow needle is fluidly connected to the plurality of fluid paths. Each hollow needle disposed within a secondary interface may be configured to puncture a top of a corresponding drug product vial when received by the secondary interface.

In an aspect, one or more of the hollow needles disposed within the secondary interfaces may have tips configured to divert a fluid flow from the diluent source towards an interior side wall of a corresponding drug product vial.

In an aspect, the adapter body may include a securing mechanism disposed within the primary interface for securely receiving the diluent source.

In an aspect, the adapter body may include a securing mechanism disposed in each of the two or more secondary interfaces for securely receiving a corresponding drug product vial.

In an aspect, the plurality of fluid paths may enable fluid flow from the diluent source received by the primary interface to the two or more drug product vials received by the two or more secondary interfaces.

In an aspect, the plurality of fluid paths may be configured such that approximately equal volumes of liquid from the diluent source flow into each of the two or more drug product vials received by the two or more secondary interfaces.

In an aspect, the adapter body may include an outlet interface that is fluidly connected to the plurality of fluid paths. The outlet interface may be configured to attach to a syringe and enable withdrawal of a drug solution from the two or more drug product vials via the plurality of fluid paths.

In an aspect, the outlet interface may be configured to attach the syringe to the plurality of fluid paths such that the drug solution is simultaneously withdrawn from the two or more drug product vials.

In an aspect, the plurality of fluid paths may include: (i) a first fluid manifold fluidly connecting the primary interface with the two or more secondary interfaces of the adapter body; and (ii) a second fluid manifold fluidly connecting the two or more secondary interfaces to the outlet interface of the adapter body.

In an aspect, the diluent source may be a pre-filled syringe and the outlet interface may also be the primary interface such that the primary interface is configured to attach to the pre-filled syringe and enable fluid flow of a diluent liquid from the pre-filled syringe to the two or more drug product vials via the plurality of fluid paths.

In an aspect, the adapter body may further define a pressure release path through the adapter body that connects ambient atmosphere with the primary interface. The adapter body may then further include: a second hollow needle disposed within the primary interface of the adapter body and fluidly connected to the pressure release path. The second hollow needle may be configured to puncture a top of the diluent vial when received by the primary interface and thereby enable air from the ambient atmosphere to enter the diluent vial.

In an aspect, the multi-vial adapter may further include a filter disposed within the pressure release path. The filter may be configured to prevent solid particulates from entering the diluent vial when received by the primary interface.

In an aspect, the adapter body may include a detachable diluent member forming the primary interface. The detachable diluent member may be configured to attach to an outlet interface of the adapter body such that the primary interface is fluidly connected with the plurality of fluid paths.

In an aspect, the outlet interface of the adapter body may be configured to attach to a syringe and withdraw a drug solution from the two or more drug product vials via the plurality of fluid paths while the detachable diluent member is detached from the adapter body.

According to another embodiment of the present disclosure, a method of reconstituting or diluting a lyophilized or concentrated drug product using a multi-vial adapter is provided. The method may include: (i) connecting at least a first diluent source containing a diluent liquid to the multi-vial adapter, wherein the first diluent source is either a diluent vial or a pre-filled syringe; (ii) connecting two or more drug product vials containing a lyophilized and/or concentrated drug product to the multi-vial adapter; (iii) transferring the diluent liquid from at least the first diluent source to the two or more drug product vials via a plurality of fluid paths through the multi-vial adapter; and (iv) withdrawing, using a drug delivery device, a reconstituted and/or diluted drug solution from the two or more drug product vials via the plurality of fluid paths through the multi-vial adapter.

In an aspect, at least the first diluent source may be a diluent vial, and the multi-vial adapter may include a primary interface having one or more securing mechanisms and one or more hollow needles disposed therein. The first diluent source may be connected to the multi-vial adapter via the primary interface such that the one or more securing mechanisms engage a top of the diluent vial to securely retain the diluent vial and the one or more hollow needles puncture the top of the diluent vial.

In an aspect, the multi-vial adapter may include two or more secondary interfaces having one or more securing mechanisms and one or more hollow needles disposed therein. The two or more drug product vials may be connected to the multi-vial adapter via a corresponding secondary interface such that the one or more securing mechanisms engage a top of each drug product vial to securely retain the corresponding drug product vial and the one or more hollow needles puncture the top of the corresponding drug product vial.

In an aspect, the method may further include: inverting the multi-vial adapter and the first diluent vial connected thereto prior to connecting the two or more drug product vials.

In an aspect, the method may further include: inverting the multi-vial adapter and the two or more drug product vials connected thereto prior to withdrawing the reconstituted and/or diluted drug solution from the two or more drug product vials.

According to yet another embodiment of the present disclosure, a drug reconstitution and/or dilution kit is provided. The kit may include: (i) a multi-vial adapter configured to reconstitute or dilute a lyophilized or concentrated drug product; and (ii) two or more drug product vials containing a lyophilized and/or concentrated drug product.

In an aspect, the drug reconstitution and/or dilution kit may further include instructions for reconstituting or diluting the lyophilized or concentrated drug product and for administering an effective dosage of the same to a subject.

In an aspect, the drug reconstitution and/or dilution kit may further include: a drug delivery device configured to connect to an outlet interface of the multi-vial adapter and withdraw a drug solution from the two or more drug product vials after reconstitution and/or dilution of the lyophilized and/or concentrated drug product.

These and other aspects of the various embodiments will be apparent from and elucidated with reference to the embodiments described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIG. 6C is a third illustration of the multi-vial adapter of FIG. 5 being used in accordance with aspects of the present disclosure.

FIG. 6D is a fourth illustration of the multi-vial adapter of FIG. 5 being used in accordance with aspects of the present disclosure.

FIG. 6E is a fifth illustration of the multi-vial adapter of FIG. 5 being used in accordance with aspects of the present disclosure.

FIG. 6F is a sixth illustration of the multi-vial adapter of FIG. 5 being used in accordance with aspects of the present disclosure.

FIG. 8E is a fifth illustration of the multi-vial adapter of FIG. 7 being used in accordance with aspects of the present disclosure.

FIG. 8F is a sixth illustration of the multi-vial adapter of FIG. 7 being used in accordance with aspects of the present disclosure.

DETAILED DESCRIPTION OF EMBODIMENTS

In accordance with various aspects of the present disclosure, adapters for simultaneously mixing two or more vials of drug products are described. As mentioned above, it is sometimes necessary to combine two or more vials of a drug product with a liquid diluent in order to obtain the proper concentration and dosage. Depending on how the manufacturer packages the drug product, the preparation process may even require diluting and/or reconstituting dozens of vials of a drug product. Accordingly, the multi-vial adapters described herein simplify the complexity of preparing and handling multiple vials of drug product, which significantly reduces preparation time, addresses dosing-related challenges like weight-based preparation, reduces drug waste issues, and reduces risks associated with maintaining sterility and avoiding contamination, among other benefits.

Figure 1:
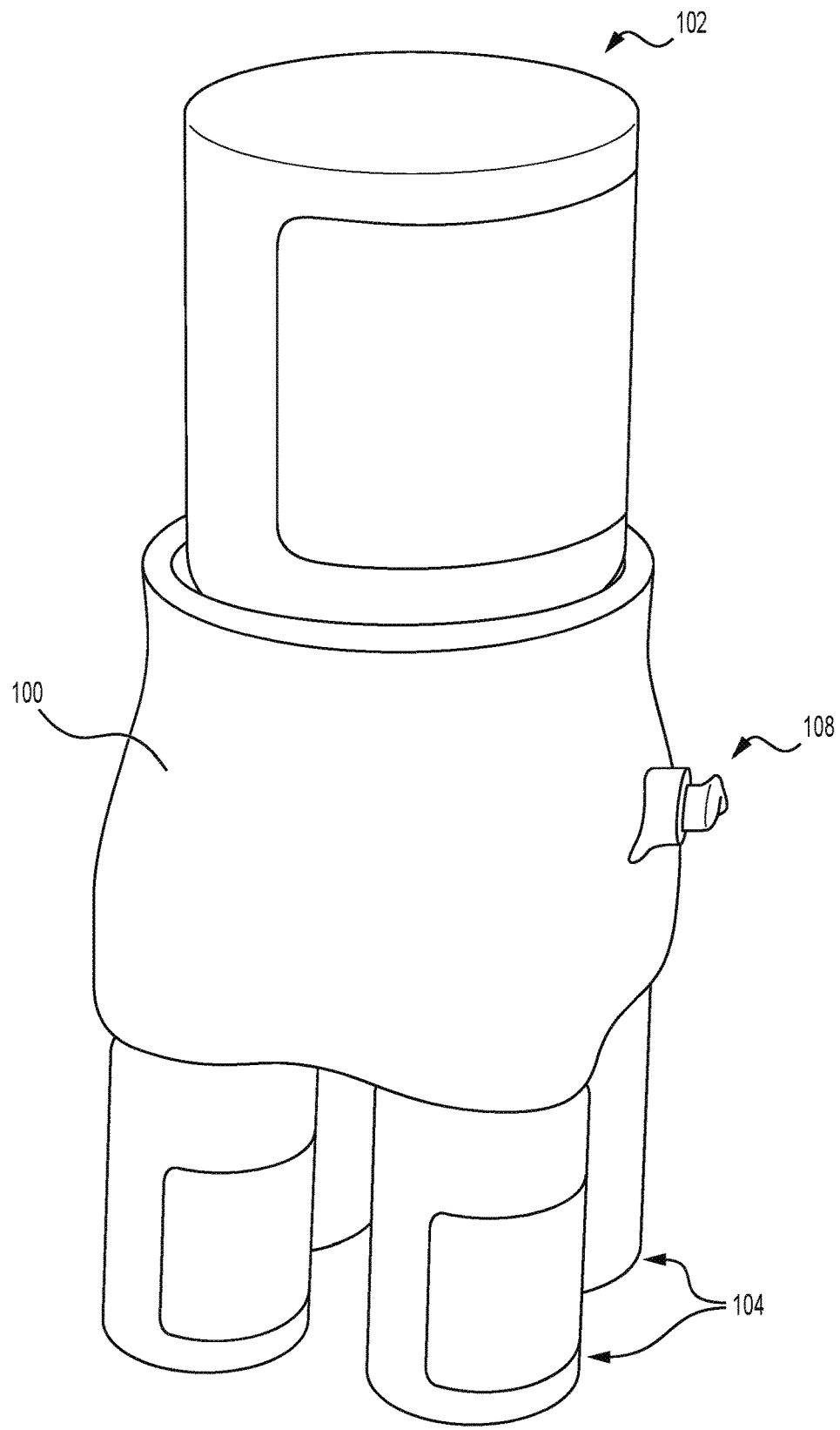
FIG. 1 is a first perspective illustration of a multi-vial adapter in use in accordance with certain aspects of the present disclosure.

With reference to FIG. 1, a multi-vial adapter 100 configured to reconstitute or dilute a lyophilized or concentrated drug product is illustrated in accordance with certain aspects of the present disclosure. As shown in the example of FIG. 1, the multi-vial adapter 100 can be configured to receive a diluent source 102 and two or more drug product vials 104. The diluent source 102 may contain a diluent liquid (e.g., diluent liquid 152) and can include a vial, a bag, a syringe, a tank, or the like. In embodiments, the multi-vial adapter 100 can be configured to receive at least two drug product vials 104. However, in specific embodiments, the multi-vial adapter 100 can be configured to receive between two and six drug product vials 104 at one time.

The multi-vial adapter 100 may provide a plurality of fluid paths or channels (e.g., fluid paths 118, 218) that enable fluid flow from the diluent source 102 to the two or more drug product vials 104. In embodiments, these fluid paths or channels through the multi-vial adapter 100 are configured such that approximately equal volumes of fluid from the diluent source 102 flows into each of the two or more drug product vials 104. In certain embodiments, the diluent fluid can include, for example and without limitation, sterile water and/or sodium chloride suitable for intramuscular, intravenous, and/or subcutaneous injection. According to aspects of the present disclosure, the diluent fluid may be provided in the diluent vial 102, which may be made from glass, a polymer material, and/or another pharmaceutically and/or physiologically inert material. Similarly, the drug product vials 104 may also be made from glass, a polymer material, and/or another pharmaceutically and/or physiological inert material. Each of the diluent vials 102 and the drug product vials 104 generally include protective tops 124, 126, which may include a cap or other type of sterile protective cover. As described in more detail below, the protective tops 124, 126 may provide one or more surfaces, ridges, or edges that engage securing mechanisms of the adapter. In particular embodiments, the diluent vials 102 and the drug product vials 104 may be single-use vials and/or single-dose vials. In further embodiments, the diluent vials 102 and/or the drug product vials 104 may also conform with ISO 8362-4:2011. However, it should be appreciated that the multi-vial adapters 100 may also be configured to receive non-standard vials as well.

In embodiments, the drug product vials 104 may contain a lyophilized and/or concentrated drug or medicament. The terms "drug" and "medicament" are defined in detail below. However, in particular embodiments, the drugs or medicaments contained in the drug product vials 104 as described herein may be used in many different types of treatments or therapies, including various enzyme replacement therapies. For example, the drug products described herein may contain an active pharmaceutical ingredient that is effective for treating Pompe disease, lysosomal acid alpha-glucosidase (GAA) deficiency, mucopolysaccharidosis, Gaucher disease, Fabry disease, and/or acid sphingomyelinase deficiency (ASMD). In specific embodiments, the enzyme replacement drugs can include, but are not limited to, Cerezyme®, Fabrazyme®, Lumizyme®, Nexviazyme®, Myozyme®, Xenpozyme®, and the like.

Figure 2:
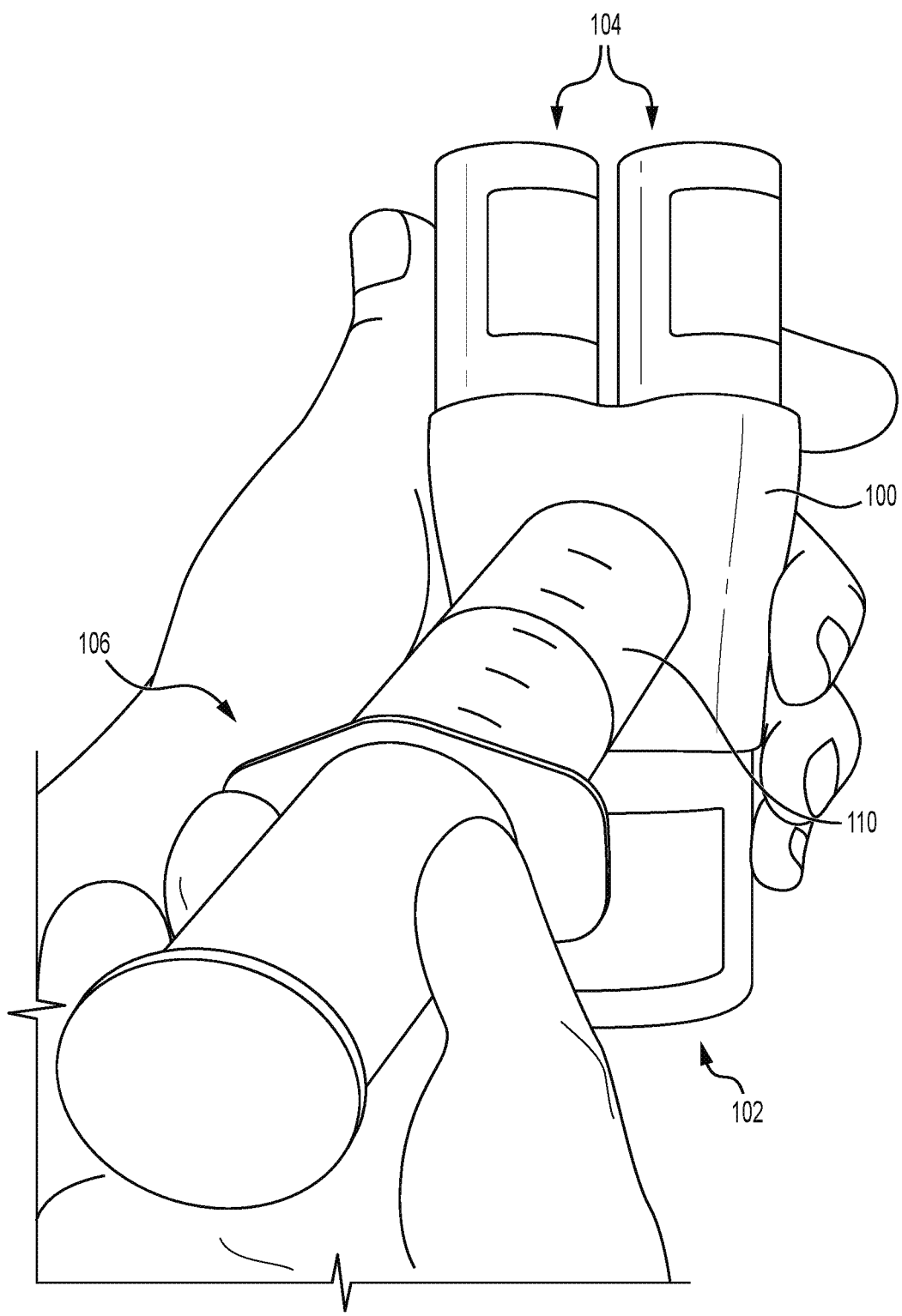
FIG. 2 is a second perspective illustration of a multi-vial adapter in use in accordance with certain aspects of the present disclosure.

The drugs and medicaments described herein may be used in connection with a drug delivery device involving a needle-based injection system. For example, as shown in FIG. 2, the multi-vial adapter 100 may enable a user to withdraw a reconstituted and/or diluted drug solution 110 from the two or more drug product vials 104 via drug delivery device 106.

As described in more detail below, the drug solution 110 may be simultaneously withdrawn from the two or more drug product vials 104 using the syringe 106 via an outlet interface, such as the outlet interface 108 shown in FIG. 1. In embodiments, the drug solution 110 may then be injected into a human or animal subject, or added to an intravenous bag for controlled infusion.

Figure 3:
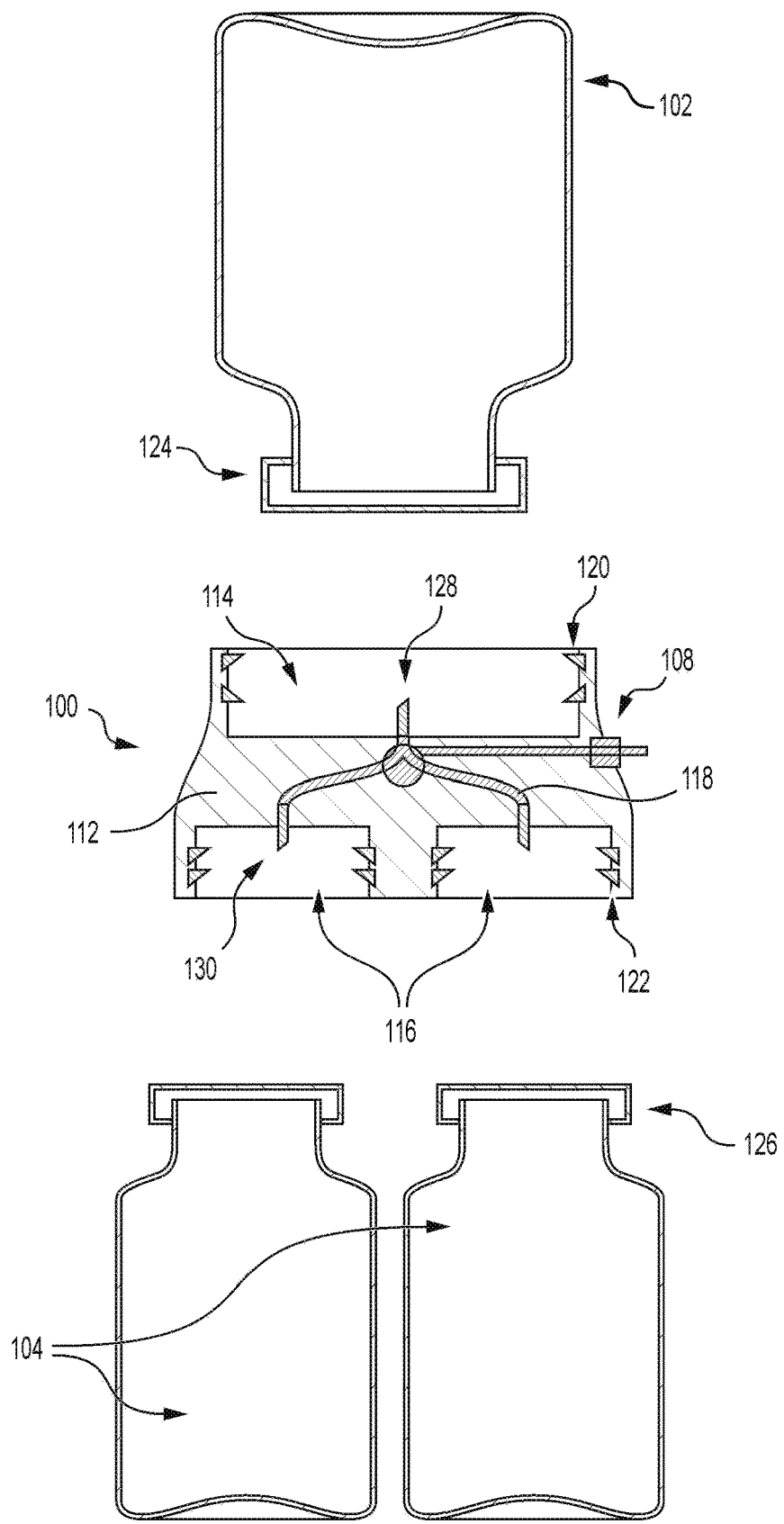
FIG. 3 is an exploded, cross-sectional illustration of a multi-vial adapter for use in accordance with aspects of the present disclosure.

With reference to FIG. 3, a cross-sectional view of a multi-vial adapter 100 of the present disclosure is illustrated in accordance with further aspects of the present disclosure. As shown in the example of FIG. 3, the multi-vial adapter 100 comprises an adapter body 112. The adapter body 112 may be manufactured from one or more types of plastics, such as a dimensionally stable plastic material that is pharmaceutically and/or physiologically inert. In particular embodiments, the adapter body 112 may be or comprise a cyclic olefin polymer (COP) or a cyclic olefin copolymer (COOP).

The adapter body 112 may be formed such that the adapter body 112 defines a number of external recesses and/or internal channels. For example, the adapter body 112 may define at least a primary interface 114 that is configured to receive a diluent source 102, and two or more secondary interfaces 116 that are configured to receive two or more drug product vials 104. As shown in FIG. 3, the primary interface 114 may be a recessed portion defined by the adapter body 112, and each of the secondary interfaces 116 may be separate recessed portions defined by an opposing side of the adapter body 112. The adapter body 112 may also define a plurality of fluid paths 118 (sometimes referred to herein as channels) through the adapter body 112. In embodiments, the plurality of fluid paths 118 fluidly connect the primary interface 114 with the two or more secondary interfaces 116, as well as the outlet interface 108.

In embodiments, the adapter body 112 may include a securing mechanism 120 disposed within the primary interface 114 for securely receiving the diluent source 102. In particular embodiments, the securing mechanism 120 may include one or a combination of hooks, tabs, protrusions, and/or ridges configured to engage a top portion 124 (e.g., the cap, etc.) of the diluent source 102 in order to hold the diluent source 102 within the primary interface 114 of the adapter body 112 during use of the multi-vial adapter 100. Similarly, the adapter body 112 may include additional securing mechanisms 122 disposed within each of the secondary interfaces 116 for securely receiving a corresponding drug product vial 104. The securing mechanisms 122 may include one or a combination of hooks, tabs, protrusions, and/or ridges configured to engage a top portion 126 (e.g., cap, etc.) of a corresponding drug product vial 104 in order to hold the corresponding drug product vial 104 within the corresponding secondary interface 116 of the adapter body 112 during use of the multi-vial adapter 100. As described herein, the securing mechanisms 120, 122 may be formed from the same material as the adapter body 112 or may be formed from a different material and added to the adapter body 112.

In particular embodiments, the adapter body 112 may include one or more securing mechanisms (e.g., protrusion arrangements 123 shown in FIG. 5, etc.) that create a detent state when a diluent source 102 and/or drug product vial 104 are received by a corresponding interface 114, 116. In particular embodiments, these detent states may be caused by plastic deformation of the securing mechanism 123 when the vials 102, 104 are received. In particular embodiments, the adapter body 112 may have securing mechanisms 123 that create more than one detent state.

In embodiments, the adapter body 112 may also include a plurality of hollow needles 128, 130 disposed within the recesses formed by the primary and/or secondary interfaces 114, 116. For example, as shown in the example of FIG. 3, the adapter body 112 can include at least one hollow needle 128 disposed within the primary interface 114. Each of the hollow needles 128 disposed within the primary interface 114 may be in fluid communication with the plurality of fluid paths 118. In particular embodiments, the hollow needles 128 disposed within the primary interface 114 are configured to puncture the top 124 of the diluent vial 102 when received by the primary interface 114.

Similarly, the adapter body 112 can include at least one hollow needle 130 disposed within each recess formed by the secondary interfaces 116. Each of the hollow needles 130 disposed within a secondary interface 116 may be in fluid communication with the plurality of fluid paths 118. In particular embodiments, the hollow needles 130 disposed with the secondary interfaces 116 are configured to puncture the top 126 of a corresponding drug product vial 104 when received by a secondary interface 116.

In some embodiments, each of the hollow needles 128, 130 (also hollow needles 144, 146, 228 described in more detail below) may be or comprise a metal and/or metal alloy. In other embodiments, the hollow needles (e.g., needles 128, 130, 144, 146, 228) may be or comprise a composite of plastic and metal, such as a plastic spike with a hollow metal liner.

Figure 4:
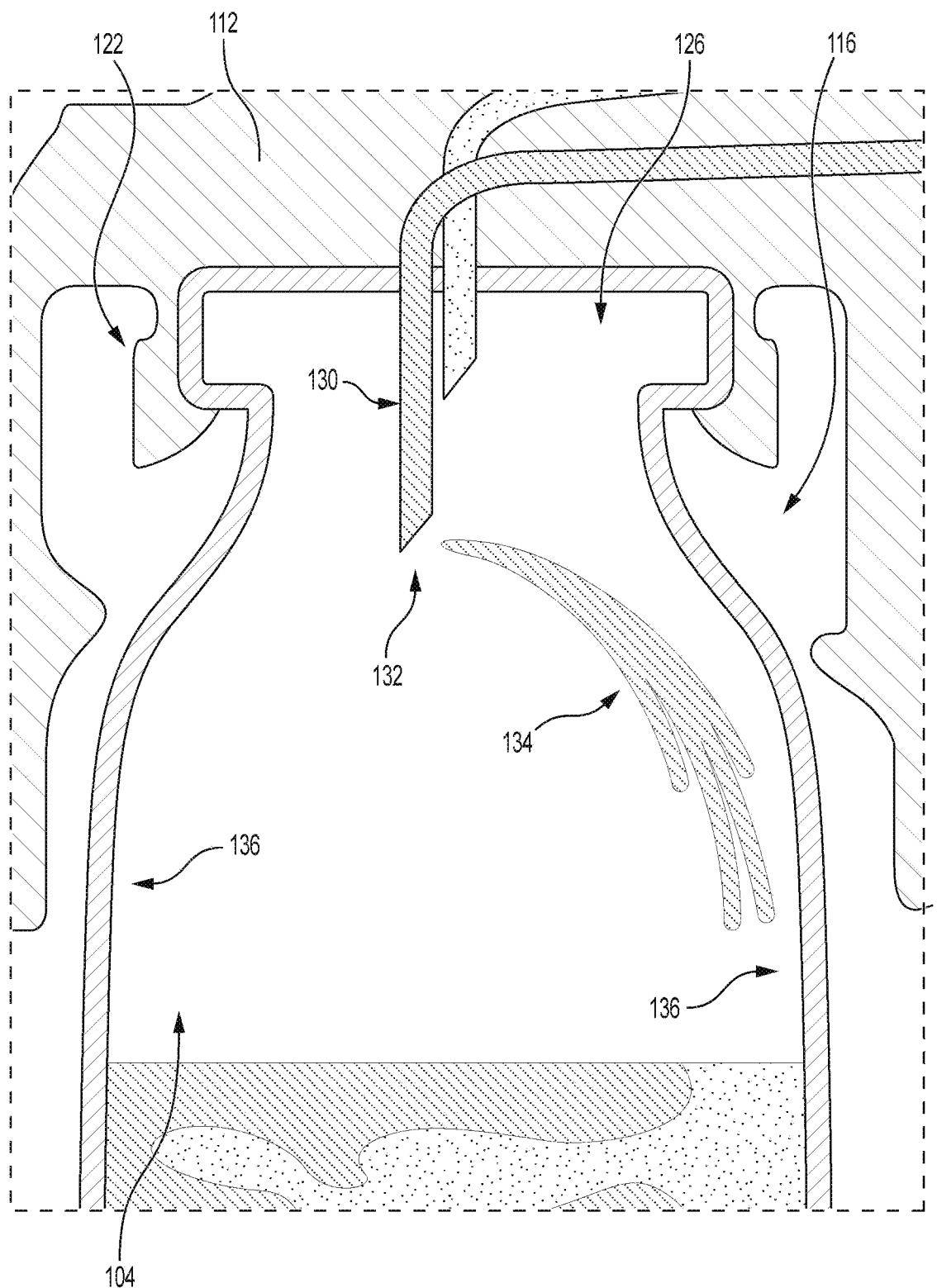
FIG. 4 is an enlarged illustration of a portion of a multi-vial adapter for use in accordance with aspects of the present disclosure.

In further embodiments, one or more of the hollow needles disposed within the recesses formed by the secondary interfaces 116 may include tips configured to divert a fluid flow from the diluent source 102 towards an interior side wall of a corresponding drug product vial 104. For example, as shown in the example of FIG. 4, a drug product vial 104 is securely received in at a secondary interface 116 defined by the adapter body 112 using a securing mechanism 122 such that the hollow needle 130 has punctured the top 126 of the drug product vial 104. In embodiments, the diluent liquid 152 may enter the drug product vials 104 via the hollow needles 130, which are in fluid communication with the plurality of fluid paths 118. In specific embodiments, the hollow needles 130 used to deliver the diluent liquid 152 to the drug product vials 104 may include a tip 132 that is configured to divert the fluid flow 134 towards an interior side wall 136 of the drug product vial 104. Because the fluid flow 134 is directed towards the side walls 136 of the drug product vials 104, damage to sensitive drugs or medicaments within the drug product vials 104 can be avoided.

As described herein, the hollow needles 128, 130 disposed within the primary and/or secondary interfaces 114, 116 may be formed from a different material as the adapter body 112. For example, in particular embodiments, the hollow needles 128, 130 may be formed from a metal or metal alloy and embedded or otherwise secured within a corresponding interface 114, 116 of the adapter body 112.

In accordance with further aspects of the present disclosure, the plurality of fluid paths 118 may include one or more distinct fluid manifolds defined as interconnected channels through the adapter body 112. For example, with reference to FIG. 5, the plurality of fluid paths 118 comprises at least a first fluid manifold 138 of multiple, interconnected fluid channels, and a second fluid manifold 140 of different, interconnected fluid channels. In embodiments, the first fluid manifold 138 may fluidly connect the primary interface 114 with the two or more secondary interfaces 116. Put another way, the first fluid manifold 138 may enable fluid flow (e.g., the diluent fluid) from the diluent source 102 received by the primary interface 114 to the two or more drug product vials 104 received by the two or more secondary interfaces 116. In further embodiments, the second fluid manifold 140 may fluidly connect the two or more secondary interfaces 116 to an outlet interface 108 of the adapter body 112. Put another way, the second fluid manifold 140 may enable fluid flow (e.g., the drug solution 110) from the two or more drug product vials 104 to an external device (e.g., a syringe 106) via the outlet interface 108.

Figure 5:
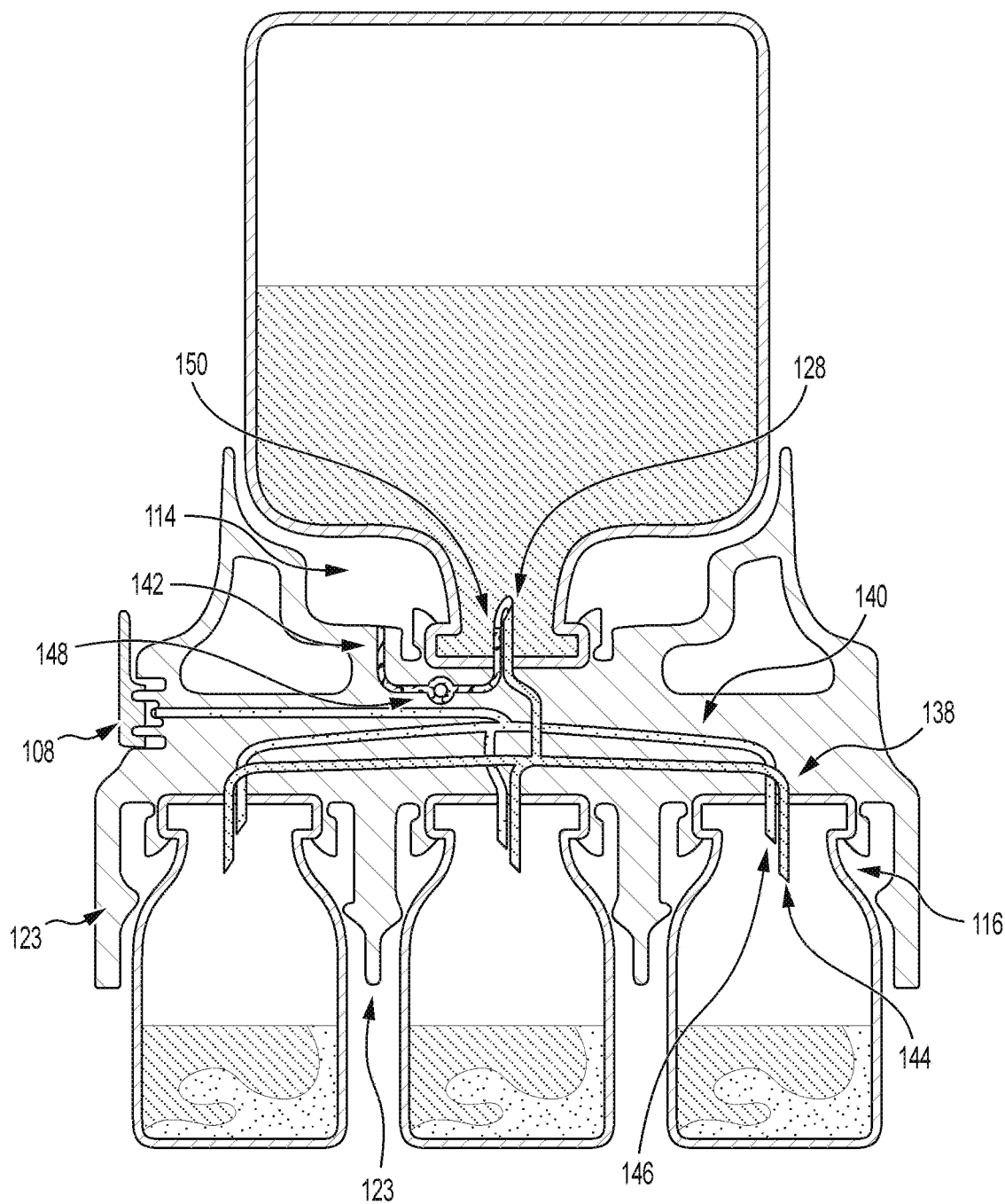
FIG. 5 is a cross-sectional illustration of one embodiment of a multi-vial adapter for use in accordance with aspects of the present disclosure.

It should be appreciated that each of the fluid manifolds 138, 140 may extend into the recesses defined by the secondary interfaces 116 via separate hollow needles 130. For example, as seen in FIG. 5, each of the secondary interfaces 116 includes a first hollow needle 144 fluidly connected to the first manifold 138, and a second hollow needle 146 fluidly connected to the second manifold 140. Thus, in certain embodiments, the adapter body 112 may include at least a first and a second needle 144, 146 disposed within each of the secondary interfaces 116 that are configured to puncture a top 126 of a corresponding drug product vial 104.

In particular embodiments, each of the fluid manifolds 138, 140 of the plurality of fluid paths 118 enable fluid flow in only one direction (e.g., from the diluent source 102 to the drug product vials 104, or from the drug product vials 104 to the outlet interface 108, etc.). However, as discussed in more detail below, it is also contemplated that the plurality of fluid paths 118 comprise a single manifold that is utilized for transferring fluid from the diluent source 102 to the drug product vials 104 and for extracting the drug solution 110 from the drug product vials 104.

As also seen in the example of FIG. 5, the plurality of fluid paths 118 may include a pressure release path 142 defined as gas-permeable or semi-permeable channel through the adapter body 112. In particular embodiments, the pressure release path 142 may connect the ambient atmosphere (i.e., the surrounding air) with the primary interface 114. Put another way, the pressure release path 142 may fluidly connect the ambient atmosphere with the interior of a diluent vial 102 when received by the primary interface 114. In embodiments, the pressure release path 142 may extend into the interior of a diluent vial 102 via an additional needle 150 disposed within the primary interface 114. In this manner, the pressure release path 142 may enable ambient air to flow into the diluent vial 102 as its liquid contents are emptied into the two or more drug product vials 104. In certain embodiments, the multi-vial adapter 100 can also include a filter 148 disposed within the pressure release path 142 that is configured to prevent solids and other particles from entering the diluent vial 102 during use of the multi-vial adapter 100.

Turning now to FIG. 6A through FIG. 6H, the steps for using one of the multi-vial adapters 100 of the present disclosure are illustrated in accordance with further aspects of the present disclosure. With respect to FIGS. 6A-6H, it should be understood that the arrows marked $F_g$ indicate the general direction of the force of gravity. As such, it should also be understood that, with respect to FIGS. 6A-6H, each of the components discussed may have a position (e.g., above or below) relative to the one or more other components.

Figure 6B:
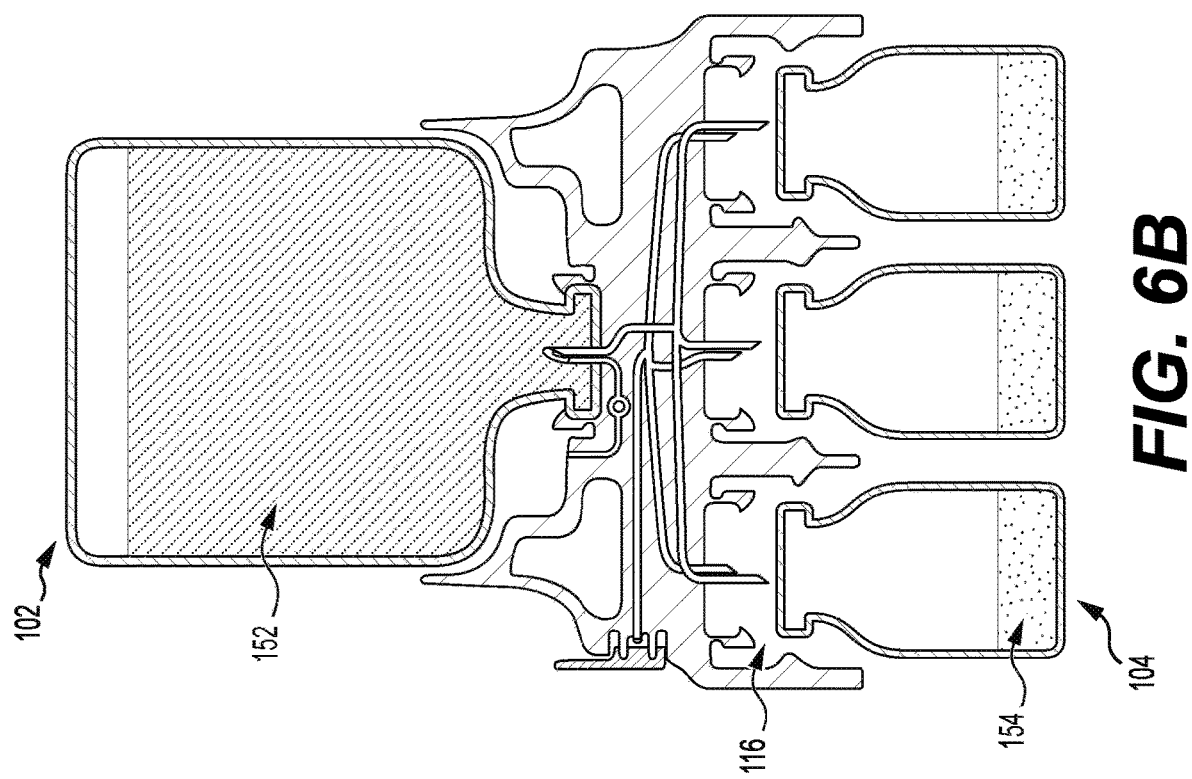
FIG. 6B is a second illustration of the multi-vial adapter of FIG. 5 being used in accordance with aspects of the present disclosure.
Figure 6A:
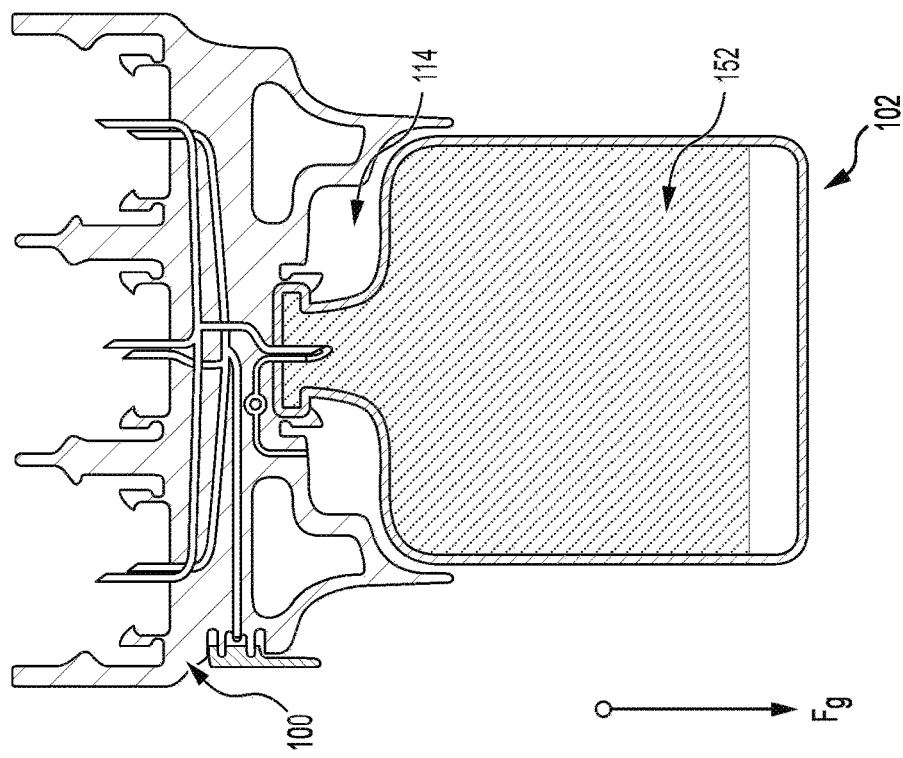
FIG. 6A is a first illustration of the multi-vial adapter of FIG. 5 being used in accordance with aspects of the present disclosure.

With reference to FIG. 6A, a first step of using the multi-vial adapter 100 is illustrated, whereby a diluent vial 102 containing a diluent liquid 152 is received by the primary interface 114 of the multi-vial adapter 100. As described above, the multi-vial adapter 100 can include one or more securing mechanisms 120 disposed within the recess defined by the primary interface 114 in order to securely receive and hold the diluent vial 102. In particular embodiments, the diluent vial 102 may be received by the primary interface 114 of the multi-vial adapter 100 by positioning the primary interface 114 over the top 124 of the diluent vial 102 and applying a downward forward such that the securing mechanism(s) 120 engage the diluent vial 102 and the one or more needles 128, 150 puncture the top 124 of the diluent vial 102.

With reference to FIG. 6B, a second step of using the multi-vial adapter 100 is illustrated, whereby the multi-vial adapter 100 is rotated and the two or more secondary interfaces 116 are positioned over two or more corresponding drug product vials 104. As discussed above, each of the drug product vials 104 may contain a drug or medicament 154, which may be a lyophilized and/or concentrated drug product. Further, it should be noted that the diluent liquid 152 is retained within the diluent vial 102 prior to engaging the two or more drug product vials 104, even though the diluent vial 102 has been inverted. Accordingly, in some embodiments, the multi-vial adapter 100 may include a valve, stopper, or other means for opening and/or closing the fluid paths 118 that enable fluid flow from the diluent vial 102, including but not limited to the stopper 156 (shown in FIG. 6D).

With reference to FIG. 6C, a third step of using the multi-vial adapter 100 is illustrated, whereby the two or more secondary interfaces 116 receive the two or more corresponding drug product vials 104 and the diluent liquid 152 begins to flow from the diluent vial 102, through the plurality of fluid paths 118, and into each of the drug product vials 104. According to certain embodiments of the present disclosure, the diluent liquid 152 may move from a rigid diluent vial 102 at atmospheric pressure to a negatively pressurized drug vial 104 through a plurality of fluid paths 118 with a continuous flow of air into the diluent vial 102 from the atmosphere communicated through a pressure release path 142. In other embodiments, the diluent liquid 152 may flow through the plurality of fluid paths 118 due to the gravity pressure head with a continuous flow of air into the diluent vial 102 from the atmosphere communicated through a pressure release path 142.

Further, as described above, the plurality of fluid paths 118 of the multi-vial adapter 100 may be configured such that approximately equal volumes of diluent liquid 152 flows into each attached drug product vial 104. This may be achieved by utilizing similar fluid path geometries in order to approximate equal flow resistances. In embodiments, the diluent liquid 152 may continue to flow into the two or more drug product vials 104 until the diluent vial 102 is emptied, as shown in the example of FIG. 6D. At this point, the drug product 154 may be fully diluted and/or reconstituted in the form of a drug solution 110, and may be ready for withdrawal.

With reference to FIG. 6E, a fourth step of using the multi-vial adapter 100 is illustrated, whereby a stopper (e.g., stopper 156 shown in FIG. 6D) is removed from the multi-vial adapter 100 and the outlet interface 108 is exposed. In particular embodiments, the outlet interface 108 may include a luer lock connection, or an alternative interface such as NRFit, a spike (male end), a septum (female end), or another non-standard, custom design interface.

With reference to FIG. 6F, a fifth step of using the multi-vial adapter 100 is illustrated, whereby a drug delivery device (such as a syringe 106) is attached to the outlet interface 108.

Figure 6G:
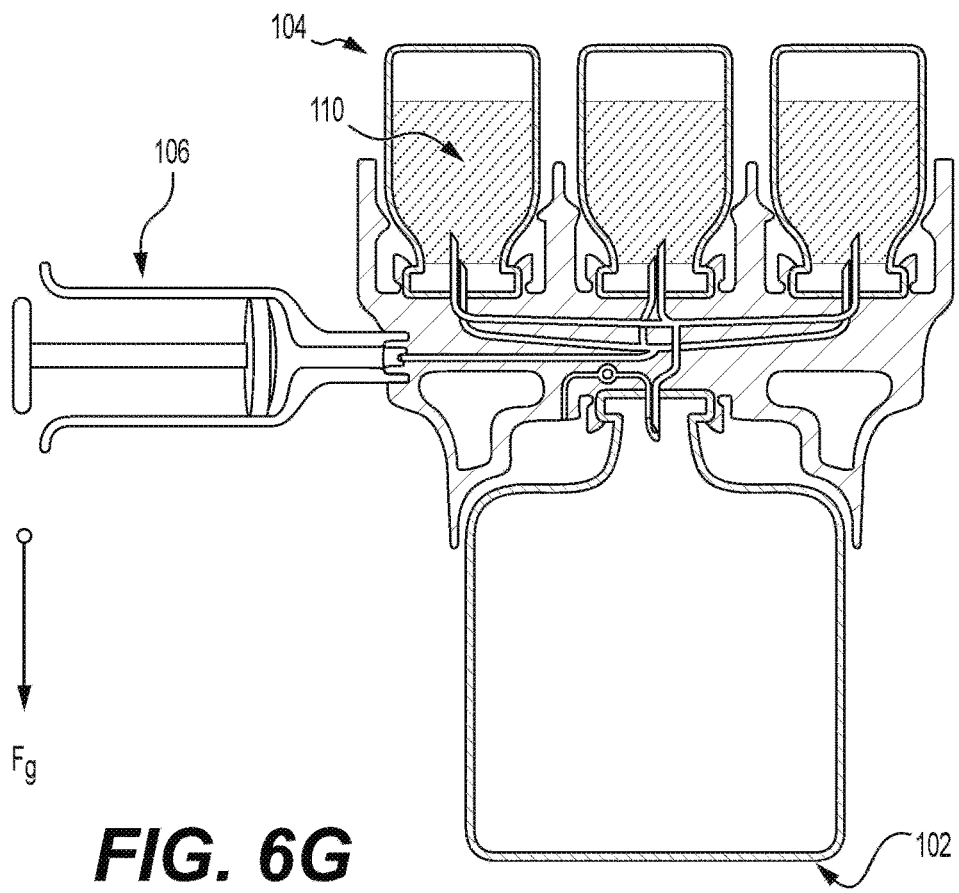
FIG. 6G is a seventh illustration of the multi-vial adapter of FIG. 5 being used in accordance with aspects of the present disclosure.

With reference to FIG. 6G, a sixth step of using the multi-vial adapter 100 is illustrated, whereby the multi-vial adapter 100 is inverted such that the drug product vials 104 containing the drug solution 110 are above the empty diluent vial 102.

Figure 6H:
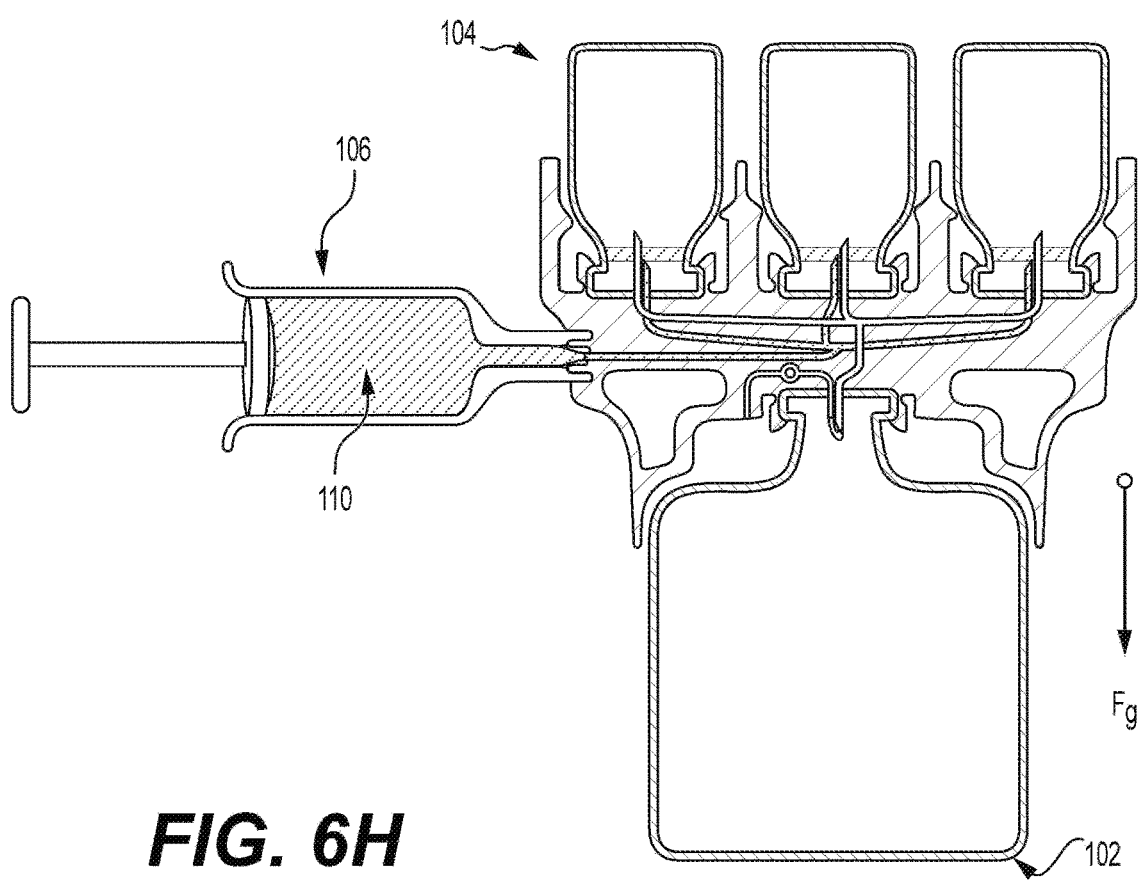
FIG. 6H is an eighth illustration of the multi-vial adapter of FIG. 5 being used in accordance with aspects of the present disclosure.

With reference to FIG. 6H, a seventh step of using the multi-vial adapter 100 is illustrated, whereby the drug delivery device (e.g., syringe 106) is used to withdraw the drug solution 110 from the two or more drug product vials 104. Once the drug solution 110 is completely withdrawn, it should be appreciated that the drug delivery device may then be detached from the outlet interface 108 and used to administer the drug solution 110 to a person or animal. In accordance with certain aspects of the present disclosure, the empty drug product vials 104, empty diluent vial 102, and the multi-vial adapter 100 may then be disposed of in the traditional manner.

Figure 7:
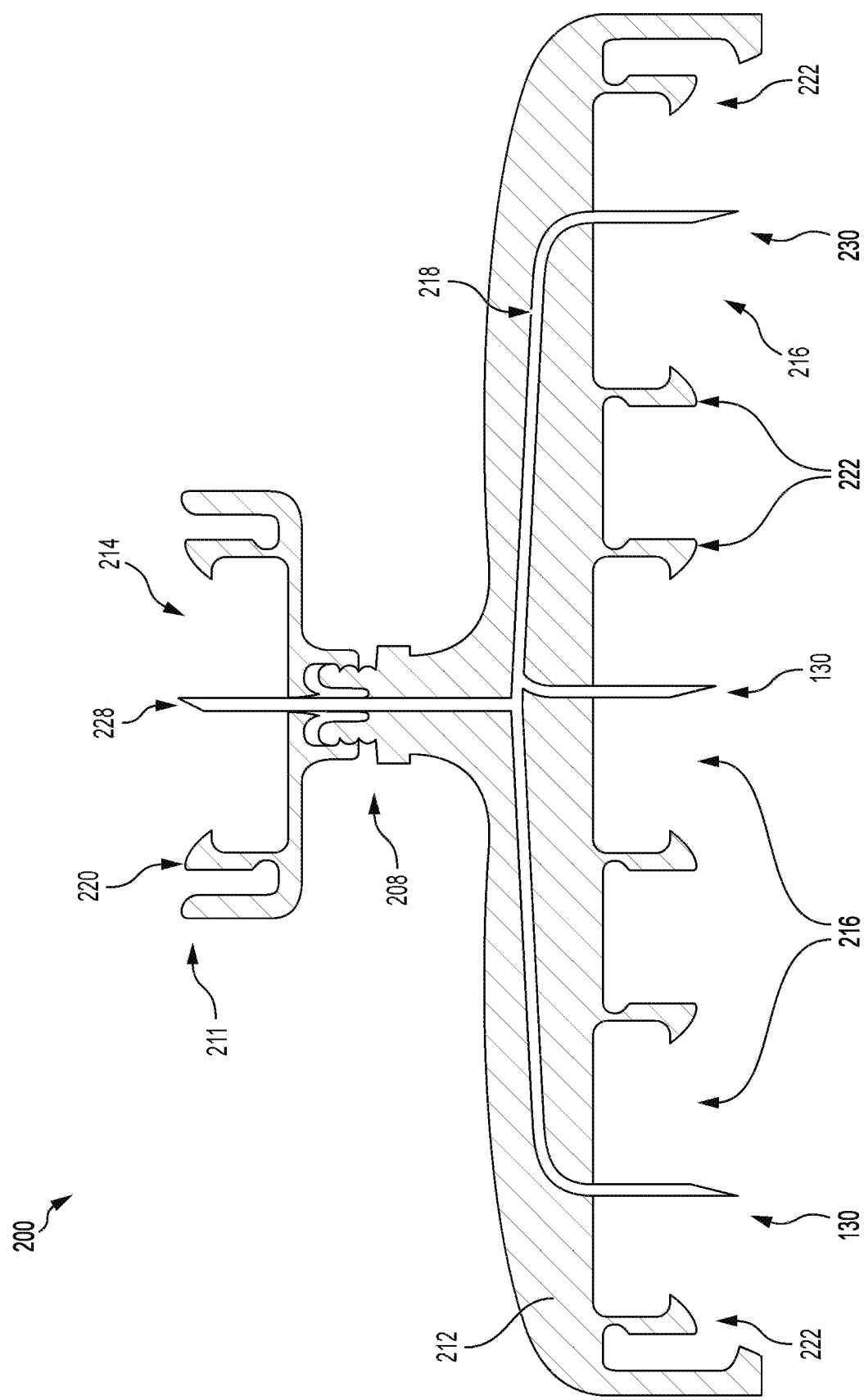
FIG. 7 is a cross-sectional illustration of another embodiment of a multi-vial adapter for use in accordance with aspects of the present disclosure.

Turning now to FIG. 7, a multi-vial adapter 200 configured to reconstitute and/or dilute a lyophilized or concentrated drug product is illustrated in accordance with another embodiment of the present disclosure. As shown, the multi-vial adapter 200 comprises an adapter body 212 having an outlet interface 208. In particular embodiments, the outlet interface 208 may include a luer lock connection, or an alternative interface such as NRFit, a spike (male end), a septum (female end), or another non-standard, custom design interface. In embodiments, the adapter body 212 may define two or more secondary interfaces 216 and a plurality of fluid paths 218 through the adapter body 212 that fluidly connect the outlet interface 208 with the two or more secondary interfaces 216. As described above, the secondary interfaces 216 (like secondary interfaces 116) are configured to receive two or more drug product vials 104.

According to certain aspects of the present disclosure, a diluent source 102 may be connected directly to the outlet interface 208 such that the diluent source 102 is fluidly connected with the plurality of fluid paths 218. For example, in some embodiments, the diluent source 102 may be a syringe 106 that is pre-filled with a diluent liquid 152, which can be connected to the outlet interface 208 and used to transfer the diluent liquid 152 to the drug product vials 104. In such embodiments, the outlet interface 208 may also be the primary interface 114.

In other embodiments, the adapter body 212 can include a detachable diluent member 211 defining a primary interface 214 that is configured to receive the diluent source 102, such as a diluent vial. As shown in the example of FIG. 7, the primary interface 214 may include a recess that is configured to receive the diluent source 102. In embodiments, the diluent member 211 may be configured to attach to the outlet interface 208 of the adapter body 212 such that the primary interface 214 is fluidly connected with the plurality of fluid paths 218. As described in more detail below, the diluent member 211 may be detached from the outlet interface 208 of the adapter body 212 such that a drug delivery device (e.g., a syringe 106, etc.) may be attached to the outlet interface 208 and used to withdraw a drug solution from the drug product vials 104.

According to the present disclosure, the detachable diluent member 211 and adapter body 212 may be manufactured from one or more types of plastics, such as a dimensionally stable plastic material that is pharmaceutically and/or physiologically inert. In particular embodiments, the adapter body 112 may be or comprise a cyclic olefin polymer (COP) or a cyclic olefin copolymer (COOP).

In embodiments, each of the primary and secondary interfaces 214, 216 of the multi-vial adapter 200 may, like the multi-vial adapter 100, include one or more securing mechanisms 220, 222. For example, as shown in the example of FIG. 7, the diluent member 211 may include a securing mechanism 220 disposed within the primary interface 214 for securely receiving a diluent vial 102. The securing mechanism 220 may include one or a combination of hooks, tabs, protrusions, and/or ridges configured to engage a top portion 124 (e.g., the cap, etc.) of the diluent vial 102 in order to hold the diluent vial 102 within the recess of the primary interface 114 during use of the multi-vial adapter 200. Similarly, the adapter body 212 may include additional securing mechanisms 222 disposed within each of the recesses of the secondary interfaces 216 for securely receiving a corresponding drug product vial 104. The securing mechanisms 222 may include one or a combination of hooks, tabs, protrusions, and/or ridges configured to engage a top portion 126 (e.g., cap, etc.) of a corresponding drug product vial 104 in order to hold the corresponding drug product vial 104 within the corresponding secondary interface 116 of the adapter body 212 during use of the multi-vial adapter 200. As described herein, the securing mechanisms 220, 222 may be formed from the same material as the adapter body 112 or may be formed from a different material and added to the diluent member 211 and/or adapter body 212.

In still further embodiments, the multi-vial adapter 200 may, like the multi-vial adapter 100, include a plurality of hollow needles 228, 230 disposed within the primary and/or secondary interfaces 214, 216. For example, as shown in the example of FIG. 7, the detachable diluent member 211 can include at least one hollow needle 228 disposed within the primary interface 214 and configured to be in fluid communication with the plurality of fluid paths 218. In particular embodiments, the hollow needle 228 may be configured to puncture the top 124 of a diluent vial 102 when received by the primary interface 214.

Similarly, the adapter body 212 can include at least one hollow needle 230 disposed within each of the secondary interfaces 216. Each of the hollow needles 230 disposed within a secondary interface 216 may be in fluid communication with the plurality of fluid paths 218. In particular embodiments, the hollow needles 230 are configured to puncture the top 126 of a corresponding drug product vial 104 when received by a secondary interface 216. As mentioned above, one or more of the hollow needles disposed within the secondary interfaces (e.g., secondary interfaces 116, 216) may include tips configured to divert a fluid flow from the diluent vial 102 towards an interior side wall 136 of a corresponding drug product vial 104.

In embodiments, the hollow needles 228, 230 may be formed from a different material as the adapter body 212 and/or detachable diluent member 211. For example, in particular embodiments, the hollow needles 228, 230 may be formed from a metal or metal alloy and embedded or otherwise secured within a corresponding interface 214, 216 of the multi-vial adapter 200.

Turning now to FIG. 8A through FIG. 8H, the steps for using one of the multi-vial adapters 200 of the present disclosure are illustrated in accordance with further aspects of the present disclosure. With respect to FIGS. 8A-8H, it should be understood that the arrows marked $F_g$ indicate the general direction of the force of gravity. As such, it should also be understood that, with respect to FIGS. 8A-8H, each of the components discussed may have a position (e.g., above or below) relative to the one or more other components.

Figure 8B:
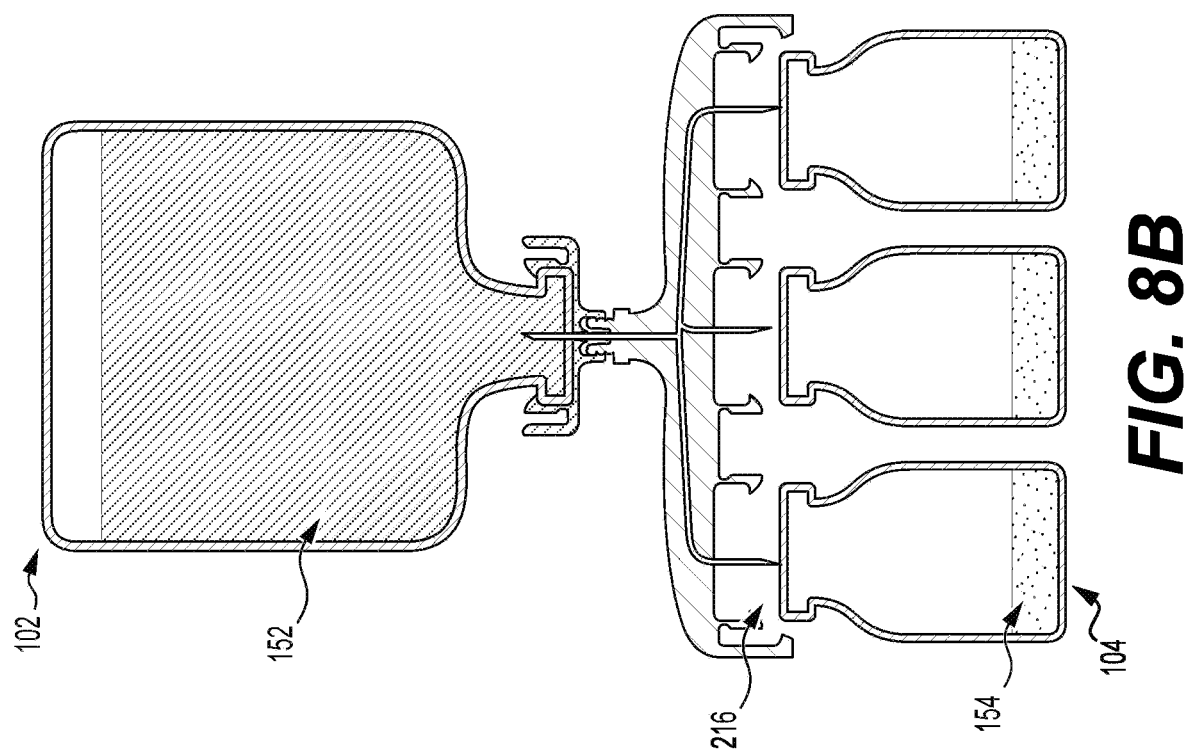
FIG. 8B is a second illustration of the multi-vial adapter of FIG. 7 being used in accordance with aspects of the present disclosure.
Figure 8A:
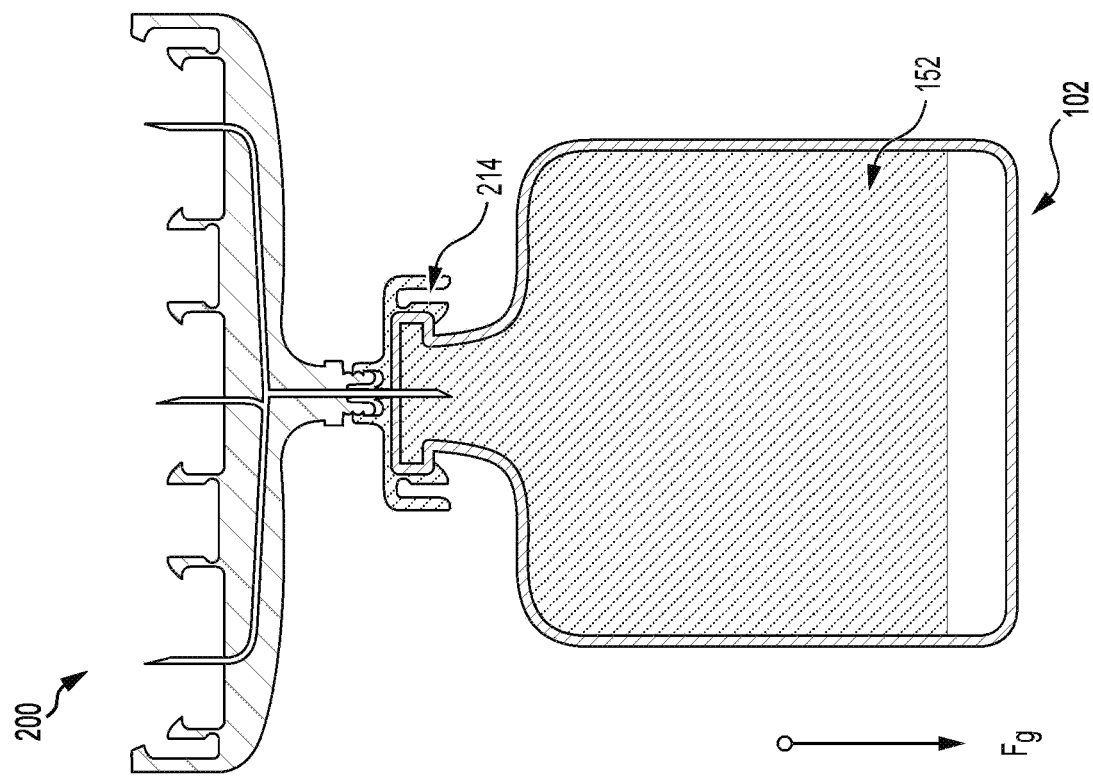
FIG. 8A is a first illustration of the multi-vial adapter of FIG. 7 being used in accordance with aspects of the present disclosure.

With reference to FIG. 8A, a first step of using the multi-vial adapter 200 is illustrated, whereby a diluent vial 102 containing a diluent liquid 152 is received by the primary interface 214 of the multi-vial adapter 200. As described above, the multi-vial adapter 200 can include one or more securing mechanisms 220 disposed within the primary interface 214 in order to securely receive and hold the diluent vial 102. In particular embodiments, the diluent vial 102 may be received by the primary interface 214 of the multi-vial adapter 200 by positioning the primary interface 214 over the top 124 of the diluent vial 102 and applying a downward forward such that the securing mechanism(s) 220 engage the diluent vial 102 and the one or more needles 228 puncture the top 124 of the diluent vial 102.

With reference to FIG. 8B, a second step of using the multi-vial adapter 200 is illustrated, whereby the multi-vial adapter 200 is inverted and the two or more secondary interfaces 216 are positioned over two or more corresponding drug product vials 104. As discussed above, each of the drug product vials 104 may contain a drug or medicament 154, which may be a lyophilized and/or concentrated drug product. Further, it should be noted that the diluent liquid 152 is retained within the diluent vial 102 prior to engaging the two or more drug product vials 104, even though the diluent vial 102 has been inverted. Accordingly, in some embodiments, the multi-vial adapter 200 may include a valve, stopper, or other means for opening and/or closing the fluid paths 218 that enabling fluid flow from the diluent vial 102.

Figure 8D:
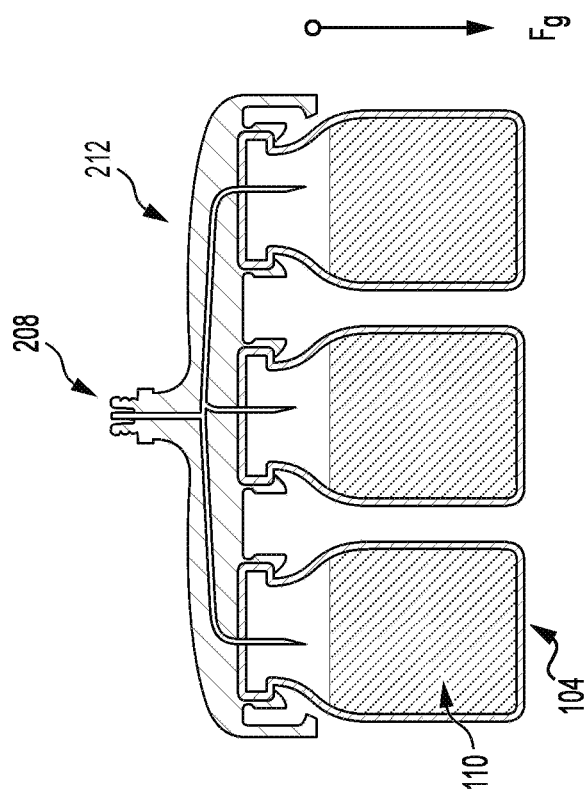
FIG. 8D is a fourth illustration of the multi-vial adapter of FIG. 7 being used in accordance with aspects of the present disclosure.
Figure 8C:
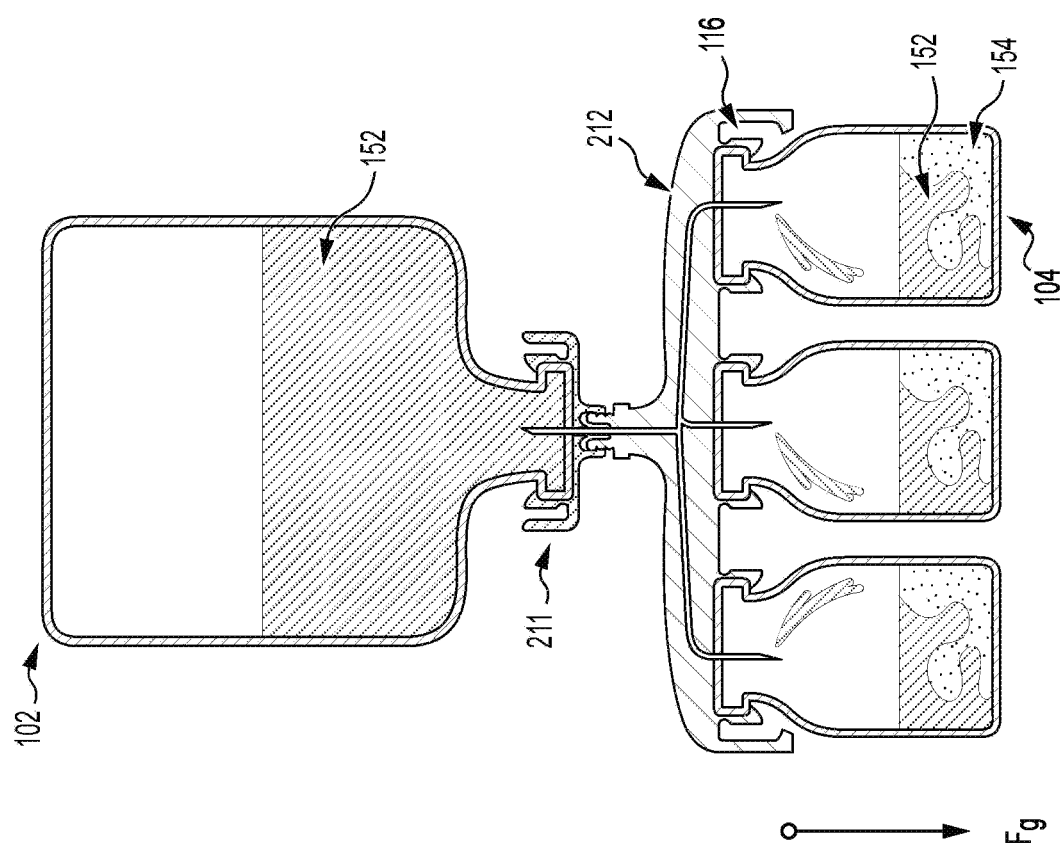
FIG. 8C is a third illustration of the multi-vial adapter of FIG. 7 being used in accordance with aspects of the present disclosure.

With reference to FIG. 8C, a third step of using the multi-vial adapter 200 is illustrated, whereby the two or more secondary interfaces 216 receive the two or more corresponding drug product vials 104 and the diluent liquid 152 begins to flow from the diluent vial 102, through the plurality of fluid paths 218, and into each of the drug product vials 104. According to certain embodiments of the present disclosure, the diluent liquid 152 may flow through the plurality of fluid paths 218 from the rigid diluent vial 102 at atmospheric pressure to a negatively pressurized drug vial 104 through equilibrium balance in pressure between the vials 102, 104 through the single manifold (i.e., one interconnected set of fluid paths 218).

Further, as described above, the plurality of fluid paths 218 of the multi-vial adapter 200 may be configured such that approximately equal volumes of diluent liquid 152 flows into each attached drug product vial 104. This may be achieved by utilizing similar fluid path geometries in order to approximate equal flow resistances. In embodiments, the diluent liquid 152 may continue to flow into the two or more drug product vials 104 until the diluent vial 102 is emptied. At this point, the drug product 154 may be fully diluted and/or reconstituted in the form of a drug solution 110, and may be ready for withdrawal.

With reference to FIG. 8D, a fourth step of using the multi-vial adapter 200 is illustrated, whereby the diluent member 211 is detached from the outlet interface 208 along with the diluent vial 102.

With reference to FIG. 8E, a fifth step of using the multi-vial adapter 200 is illustrated, whereby a drug delivery device (such as a syringe 106) is attached to the outlet interface 208. In particular embodiments, the outlet interface 208 may include a luer lock connection, or an alternative interface such as NRFit, a spike (male end), a septum (female end), or another non-standard, custom design interface. In further embodiments, the drug delivery device (e.g., syringe 106) can have a complementary connection interface.

With reference to FIG. 8F, a sixth step of using the multi-vial adapter 200 is illustrated, whereby air is introduced into the drug product vials 104 using the drug delivery device 106 via the plurality of fluid paths 218. That is, the drug product vials 104 are pressurized using the drug delivery device 106.

Figure 8H:
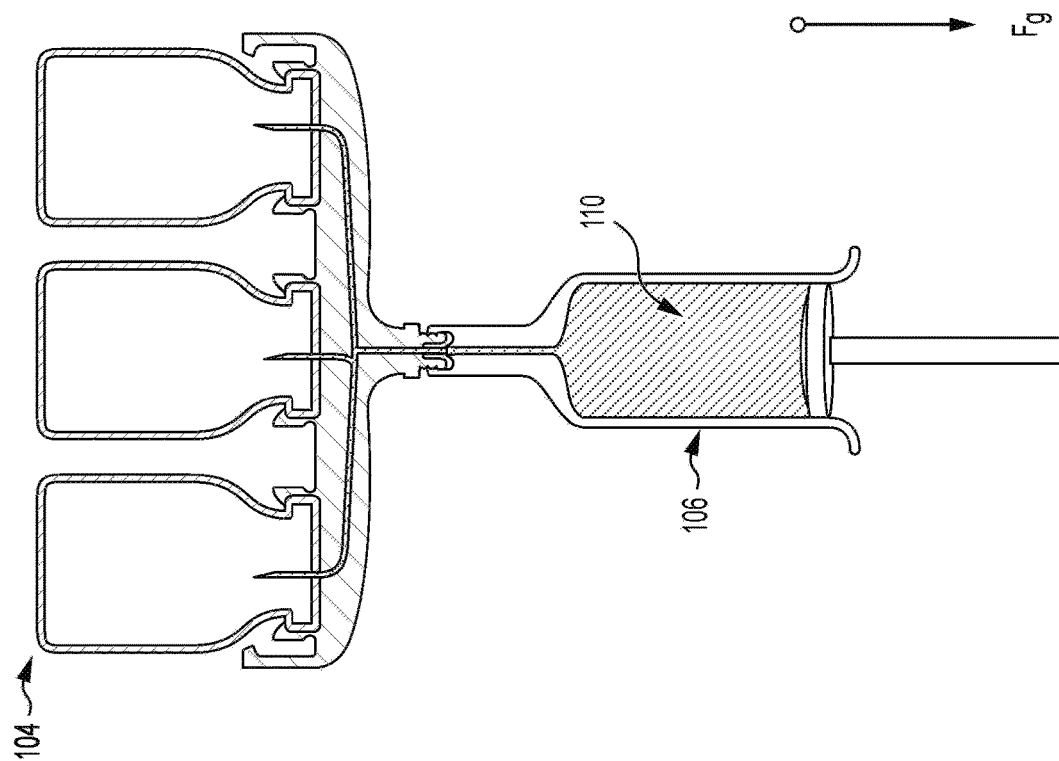
FIG. 8H is an eighth illustration of the multi-vial adapter of FIG. 7 being used in accordance with aspects of the present disclosure.
Figure 8G:
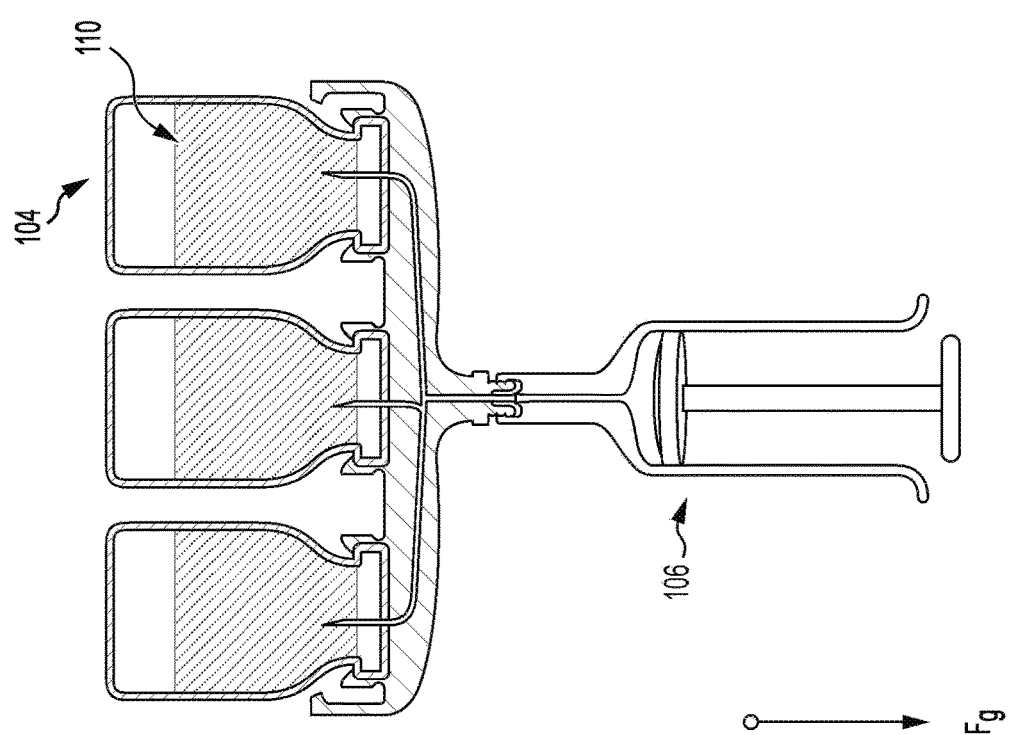
FIG. 8G is a seventh illustration of the multi-vial adapter of FIG. 7 being used in accordance with aspects of the present disclosure.

With reference to FIG. 8G, a seventh step of using the multi-vial adapter 200 is illustrated, whereby the multi-vial adapter 200 is inverted, along with the drug product vials 104, while the drug product vials 104 are pressurized.

With reference to FIG. 8H, an eighth step of using the multi-vial adapter 200 is illustrated, whereby the drug delivery device (e.g., syringe 106) is used to withdraw the drug solution 110 from the two or more drug product vials 104. Once the drug solution 110 is completely withdrawn, it should be appreciated that the drug delivery device may then be detached from the outlet interface 208 and used to administer the drug solution 110 to a person or animal. In accordance with certain aspects of the present disclosure, the empty drug product vials 104, empty diluent vial 102, and the multi-vial adapter 200 may then be disposed of in the traditional manner.

Figure 9:
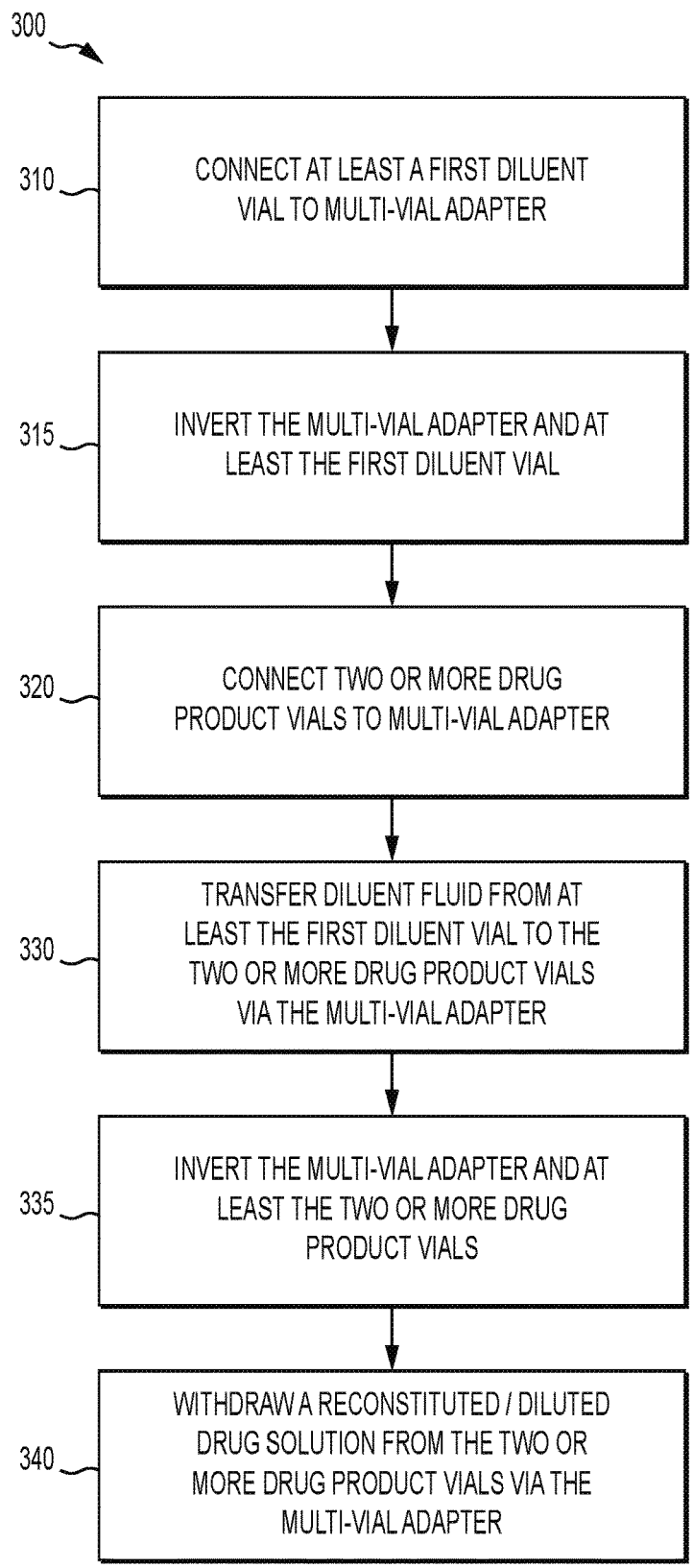
FIG. 9 is a flowchart illustrating a method of reconstituting or diluting a lyophilized or concentrated drug product using a multi-vial adapter in accordance with aspects of the present disclosure.

Turning now to FIG. 9, a method 300 of reconstituting or diluting a lyophilized or concentrated drug product using a multi-vial adapter 100, 200 is illustrated in accordance with various aspects of the present disclosure. In particular embodiments, the method 300 may include one or more steps of described above with respect to FIGS. 6A-6H and/or FIGS. 8A-8H. In specific embodiments, the method 300 includes at least the following: in a step 310, connecting at least a first diluent source 102 containing a diluent liquid 152 to the multi-vial adapter 100, 200; in a step 320, connecting two or more drug product vials 104 containing a lyophilized and/or concentrated drug product 154 to the multi-vial adapter 100, 200; in a step 330, transferring the diluent liquid 152 from at least the first diluent source 102 to the two or more drug product vials 104 via a plurality of fluid paths 118, 218 through the multi-vial adapter 100, 200; and in a step 340, withdrawing, using a drug delivery device 106, a reconstituted and/or diluted drug solution 110 from the two or more drug product vials 104 via the plurality of fluid paths 118, 218 through the multi-vial adapter 100, 200. In particular embodiments, the diluent source 102 may be a syringe (e.g., syringe 106) or a vial (e.g., vial 102) that is pre-filled with the diluent liquid 152.

In particular embodiments, the diluent source 102 may be a diluent vial, and the multi-vial adapter 100, 200 may include a primary interface 114, 214 configured to receive at least one such diluent vial 102. Accordingly, the step 310 may include connecting first diluent vial 102 containing a diluent liquid 152 to the multi-vial adapter 100, 200 such that the first diluent vial 102 is received at a primary interface 114, 214 of the multi-vial adapter 100, 200. When a diluent vial 102 is received by the primary interface 114, 214 of a multi-vial adapter 100, 200 in accordance with the present disclosure, one or more securing mechanisms 120, 220 may be engaged by the diluent vial 102 to securely retain the diluent vial 102 within the primary interface 114, 214. Further, when a diluent vial 102 is received by the primary interface 114, 214 of a multi-vial adapter 100, 200 in accordance with the present disclosure, one or more hollow needles 128, 150, 228 disposed within the primary interface of the multi-vial adapter may puncture a top 124 of the diluent vial 102.

In other embodiments, the diluent source 102 may be a syringe 106 or similar device that is pre-filled with a diluent liquid 152. In such embodiments, the outlet interface 108, 208 may also be the primary interface 114, 214 whereby the syringe 106 is connected and the diluent liquid 152 is introduced to the drug product vials 104.

According to the step 320, the method 300 may include connecting two or more drug product vials 104 containing a lyophilized and/or concentrated drug product 154 to the multi-vial adapter 100, 200 such that the two or more drug product vials 104 are received by a corresponding number of secondary interfaces 116, 216. When a drug product vial 104 is received by a secondary interface 116, 216 of a multi-vial adapter 100, 200 in accordance with the present disclosure, one or more securing mechanisms 122, 123, 222 may be engaged by the drug product vial 104 to securely retain the drug product vial 104 within the corresponding secondary interface 116, 216. Further, when a drug product vial 104 is received by a secondary interface 116, 216 of a multi-vial adapter 100, 200 in accordance with the present disclosure, one or more hollow needles 144, 146, 230 disposed within the corresponding secondary interface 116, 216 of the multi-vial adapter 100, 200 may puncture a top 126 of a corresponding drug product vial 104.

Then, the method 300 can include, in a step 330, transferring the contents (e.g., the diluent liquid 152) from the diluent vial 102 to the two or more drug product vials 104 via a plurality of fluid paths 118, 218 through the multi-vial adapter 100, 200. According to certain embodiments of the present disclosure, the diluent liquid 152 may move from a diluent source 102 at atmospheric pressure to a negatively pressurized drug vial 104 through a plurality of fluid paths 118 with a continuous flow of air into the diluent vial 102 from the atmosphere communicated through a pressure release path 142. In other embodiments, the diluent liquid 152 may flow through the plurality of fluid paths 118 due to the gravity pressure head with a continuous flow of air into the diluent vial 102 from the atmosphere communicated through a pressure release path 142. In further embodiments, the diluent source 102 may be a syringe 106 and the diluent liquid 152 may move from the syringe 106 to the drug vials 104 by ejecting the diluent liquid 152 from the syringe 106.

In embodiments, the plurality of fluid paths 118, 218 of the multi-vial adapter 100, 200 may be configured such that approximately equal volumes of diluent liquid 152 flows into each attached drug product vial 104. This may be achieved by utilizing similar fluid path geometries in order to approximate equal flow resistances. In embodiments, the diluent liquid 152 may continue to flow into the two or more drug product vials 104 until the diluent source 102 is emptied.

In embodiments, the hollow needles 130, 230 used to deliver the diluent liquid 152 to the drug product vials 104 may include tips (e.g., tips 132) that are configured to divert the fluid flow 134 towards an interior side wall 136 of the drug product vial 104. Because the fluid flow 134 is directed towards the side walls 136 of the drug product vials 104, damage to sensitive drugs or medicaments within the drug product vials 104 can be avoided.

In a step 340, the method 300 can include withdrawing a reconstituted and/or diluted drug solution 110 from the two or more drug product vials 104 via the plurality of fluid paths 118, 218 through the multi-vial adapter 100, 200. In embodiments, the drug solution 110 may be withdrawn using a drug delivery device 106. The drug delivery device can include, but is not limited to, a syringe 106. In particular embodiments, the syringe 106 may be connected to an outlet interface 108, 208 of the multi-vial adapter 100, 200 that fluidly connects the syringe 106 to the drug product vials 104 via at least a portion of the plurality of fluid paths 118, 218.

In some embodiments, the method 300 may further include, in a step 315, inverting the multi-vial adapter 100, 200 and at least the first diluent vial 102 connected thereto prior to connecting the two or more drug product vials 104. For example, as shown in FIG. 6A and FIG. 6B, the multi-vial adapter 100 is inverted 180° after the diluent vial 102 is connected. Similarly, as shown in FIG. 8A and FIG. 8B, the multi-vial adapter 200 is inverted 180° after the diluent vial 102 is connected.

In further embodiments, the method 300 may further include, in a step 335, inverting the multi-vial adapter 100, 200 and the two or more drug product vials 104 connected thereto prior to withdrawing the reconstituted and/or diluted drug solution 110 from the two or more drug product vials 104. For example, as shown in FIGS. 6G and 6H, the multi-vial adapter 100 is inverted 180° and the syringe 106 is used to withdraw the drug solution 110 via the plurality of fluid paths 118. However, it should be appreciated that the syringe 106 may be attached to the multi-vial adapter 100, 200 prior to this inversion step, as shown in FIG. 6E and FIG. 6F.

Similarly, as shown in FIGS. 8D and 8E, a detachable diluent member 211 may be disconnected from the adapter body 212 to open access to the outlet interface 208 and enable withdrawal of the drug solution 110. As shown in FIG. 8E and FIG. 8F, the syringe 106 may be used to introduce air into the drug product vials 104 prior to inverting the multi-vial adapter 200. Then, as shown in FIGS. 8G and 8H, the multi-vial adapter 200 and the drug product vials 104 are inverted 180° and the drug solution 100 is withdrawn from the drug product vials 104 through the plurality of fluid paths 218.

Figure 10:
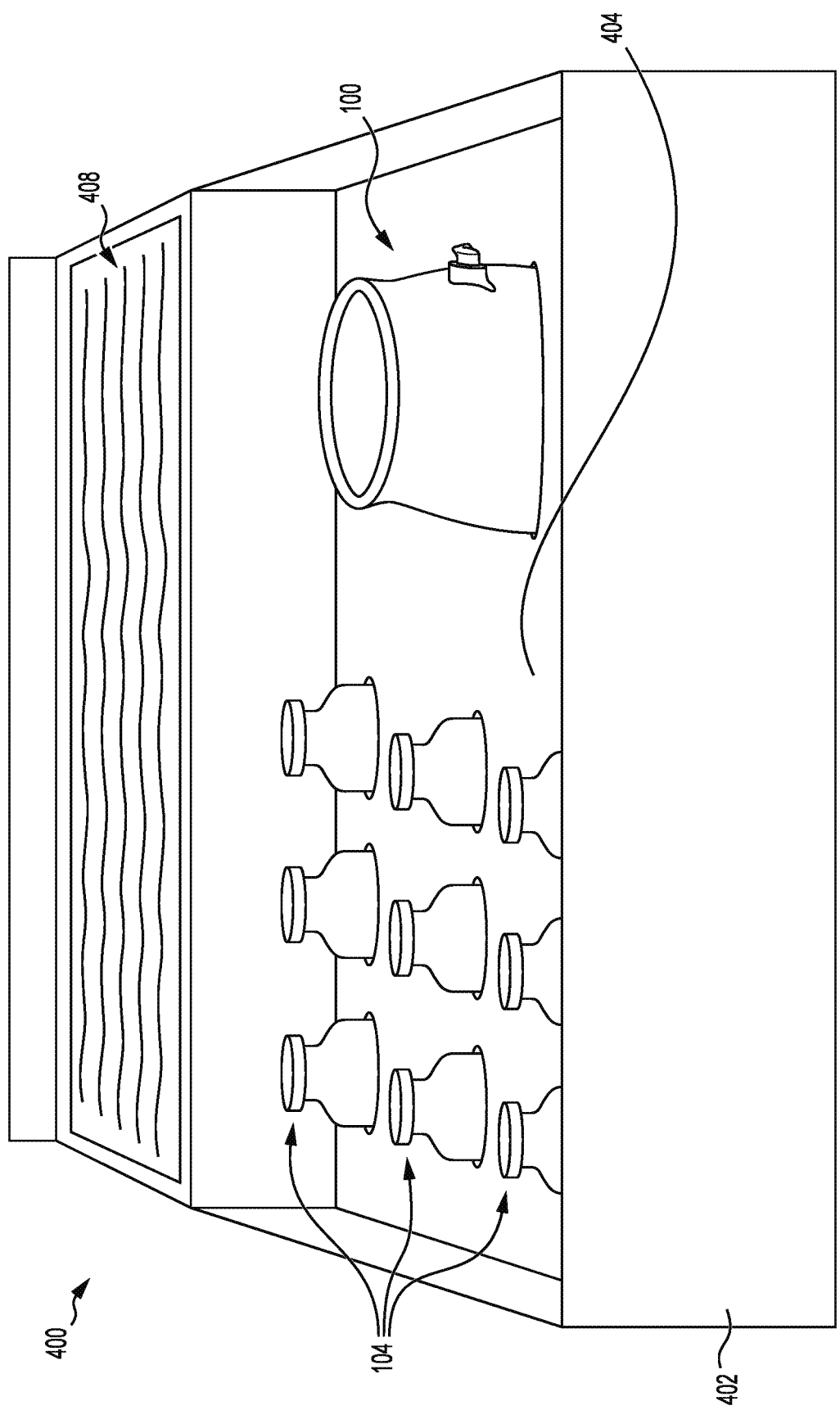
FIG. 10 is an illustration of a drug reconstitution and/or dilution kit in accordance with aspects of the present disclosure.

Also provided herein are preparation kits for reconstituting and/or diluting a lyophilized and/or concentrated drug product as described above. For example, with reference to FIG. 10, a sample kit 400 is illustrated in accordance with certain aspects of the present disclosure. As shown, the kit 400 may include one or more multi-vial adapters (e.g., adapters 100, 200), and two or more drug product vials 104 containing a lyophilized and/or concentrated drug product 154. In embodiments, the multi-vial adapters (e.g., adapters 100, 200) may be wrapped or otherwise provided within sterile packaging. In further embodiments, the multi-vial adapter(s) 100, 200 and the drug product vials 104 may be provided in a box 402 or other sterile packaging. A packing material 404 may be provided within the kit 400 in order to secure and protect the contents thereof.

In embodiments, the kit 400 may further include instructions 408 for reconstituting or diluting the lyophilized or concentrated drug product and for administering an effective dosage of the same to a subject. Although not shown, the kit 400 may also include other components related to the use/administration of the drug products 154. For example, in some embodiments, the kit 400 may also include one or more diluent vials 102 containing a diluent liquid 152 and/or one or more drug delivery devices (e.g., a syringe 106) that is configured to connect to the outlet interface 108, 208 of the multi-vial adapter(s) 100, 200.

As described herein, each preparation kit 400 may include one or multiple doses of a medicament, e.g., to form an injectable liquid medicament customized for a patient. The methods described herein (e.g., method 300) may be used in the preparation of an injectable liquid medicament using the preparation kit 400. In particular embodiments, the preparation kit 400 may include drug product comprising an active pharmaceutical ingredient that may be used to treat at least one of the following conditions: Pompe disease, lysosomal acid alpha-glucosidase (GAA) deficiency, mucopolysaccharidosis, Gaucher disease, Fabry disease, and acid sphingomyelinase deficiency (ASMD). For example, in various embodiments, the preparation kit 400 may include a lyophilized and/or concentrated form of one of the following: Cerezyme®, Fabrazyme®, Lumizyme®, Nexviazyme®, Myozyme®, and Xenpozyme®.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydurcon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"); Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014(E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

As used herein, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A multi-vial adapter configured to reconstitute or dilute a lyophilized or concentrated drug product, the multi-vial adapter comprising:
an adapter body comprising: (i) a primary interface configured to receive a diluent source containing a diluent liquid, (ii) two or more secondary interfaces connected in parallel with the primary interface and configured to receive two or more drug product vials that contain a drug product, and (iii) an outlet interface, wherein the adapter body defines a plurality of fluid paths through the adapter body that fluidly connect the primary interface with the two or more secondary interfaces and fluidly connect the two or more secondary interfaces with the outlet interface, and wherein the outlet interface enables withdrawal of a drug solution comprising the diluent liquid and the drug product from the two or more drug product vials via the plurality of fluid paths;
wherein the diluent source is either a diluent vial or a pre-filled syringe; and
wherein the plurality of fluid paths are configured to enable a simultaneous fluid flow of the diluent liquid from the diluent source received by the primary interface to the two or more drug product vials received by the two or more secondary interfaces.

2. The multi-vial adapter of claim 1, wherein the diluent source is a diluent vial and the adapter body comprises at least one hollow needle disposed within the primary interface such that the at least one hollow needle is fluidly connected to the plurality of fluid paths, the at least one hollow needle being configured to puncture a top of the diluent vial when received by the primary interface.

3. The multi-vial adapter of claim 2, wherein the adapter body further defines a pressure release path through the adapter body that connects ambient atmosphere with the primary interface, and wherein the adapter body further comprises:
a second hollow needle disposed within the primary interface of the adapter body and fluidly connected to the pressure release path, wherein the second hollow needle is configured to puncture a top of the diluent vial when received by the primary interface and thereby enable air from the ambient atmosphere to enter the diluent vial.

4. The multi-vial adapter of claim 3, wherein the multi-vial adapter further comprises a filter disposed within the pressure release path, the filter configured to prevent solid particulates from entering the diluent vial when received by the primary interface.

5. The multi-vial adapter of claim 1, wherein the plurality of fluid paths are configured such that approximately equal volumes of liquid from the diluent source flow into each of the two or more drug product vials received by the two or more secondary interfaces.

6. The multi-vial adapter of claim 1, wherein the adapter body comprises at least one hollow needle disposed within each of the two or more secondary interfaces, each hollow needle being fluidly connected to the plurality of fluid paths, and wherein each hollow needle disposed within a secondary interface is configured to puncture a top of a corresponding drug product vial when received by the secondary interface.

7. The multi-vial adapter of claim 6, wherein one or more of the hollow needles disposed within the secondary interfaces have tips configured to divert a fluid flow from the diluent source towards an interior side wall of a corresponding drug product vial.

8. The multi-vial adapter of claim 1, wherein the adapter body comprises a securing mechanism disposed within the primary interface for securely receiving the diluent source.

9. The multi-vial adapter of claim 1, wherein the adapter body comprises a securing mechanism disposed in each of the two or more secondary interfaces for securely receiving a corresponding drug product vial.

10. The multi-vial adapter of claim 1, wherein the outlet interface is configured to attach to a syringe.

11. The multi-vial adapter of claim 10, wherein the outlet interface is configured to attach the syringe to the plurality of fluid paths such that the drug solution is simultaneously withdrawn from the two or more drug product vials.

12. The multi-vial adapter of claim 10, wherein the plurality of fluid paths comprises:
a first fluid manifold fluidly connecting the primary interface with the two or more secondary interfaces of the adapter body; and
a second fluid manifold fluidly connecting the two or more secondary interfaces to the outlet interface of the adapter body.

13. The multi-vial adapter of claim 10, wherein the diluent source is a pre-filled syringe and the outlet interface is also the primary interface such that the primary interface is configured to attach to the pre-filled syringe and enable fluid flow of a diluent liquid from the pre-filled syringe to the two or more drug product vials via the plurality of fluid paths.

14. The multi-vial adapter of claim 1, wherein the adapter body comprises a detachable diluent member forming the primary interface, the detachable diluent member being configured to attach to an outlet interface of the adapter body such that the primary interface is fluidly connected with the plurality of fluid paths.

15. The multi-vial adapter of claim 14, wherein the outlet interface of the adapter body is configured to attach to a syringe and withdraw a drug solution from the two or more drug product vials via the plurality of fluid paths while the detachable diluent member is detached from the adapter body.

* * * * *